US008252971B2

(12) United States Patent
Aali et al.

(10) Patent No.: US 8,252,971 B2
(45) Date of Patent: Aug. 28, 2012

(54) SYSTEMS AND METHODS FOR PROTECTING INCISIONS

(75) Inventors: Adel Aali, Irvine, CA (US); Raymond Barbuto, Dagsboro, DE (US)

(73) Assignee: Aalnex, Inc., Irvine, CA (US)

( * ) Notice: Subject to any disclaimer, the term of this patent is extended or adjusted under 35 U.S.C. 154(b) by 511 days.

(21) Appl. No.: 12/504,590

(22) Filed: Jul. 16, 2009

(65) Prior Publication Data

US 2011/0015557 A1   Jan. 20, 2011

(51) Int. Cl.
*A61F 13/00* (2006.01)
*A61F 15/00* (2006.01)

(52) U.S. Cl. .......................................... 602/56; 604/304

(58) Field of Classification Search ............... 602/41–58; 604/289, 290, 304–308, 540; 128/888–889
See application file for complete search history.

(56) References Cited

U.S. PATENT DOCUMENTS

| | | |
|---|---|---|
| 2,148,882 A | 2/1939 | Scholl |
| 2,273,873 A | 2/1942 | Klein |
| 2,305,289 A | 12/1942 | Coburg |
| 2,367,690 A | 1/1945 | Purdy |
| 2,443,140 A | 6/1948 | Larsen |
| 2,443,481 A | 6/1948 | Séné |
| 3,026,874 A | 3/1962 | Stevens |
| 3,334,626 A | 8/1967 | Schimmel |
| 3,610,238 A | 10/1971 | Rich |
| 4,023,569 A | 5/1977 | Warnecke et al. |
| 4,181,127 A | 1/1980 | Linsky et al. |
| 4,212,296 A | 7/1980 | Schaar |
| 4,252,120 A | 2/1981 | Carpenter |
| 4,399,816 A | 8/1983 | Spangler |
| 4,726,364 A | 2/1988 | Wylan |
| 4,969,881 A | 11/1990 | Viesturs |
| 4,972,829 A | 11/1990 | Knerr |
| 5,020,547 A | 6/1991 | Strock |

(Continued)

FOREIGN PATENT DOCUMENTS

DE        519353 C      9/1931

(Continued)

OTHER PUBLICATIONS

USPTO Notice of Allowance for U.S. Appl. No. 11/409,364, 7 pages (mailed Jul. 10, 2009).

(Continued)

*Primary Examiner* — Kim M Lewis
*Assistant Examiner* — Tarla Patel
(74) *Attorney, Agent, or Firm* — Jones Day; Nicola A. Pisano; Jaime D. Choi

(57) ABSTRACT

The present invention provides systems and methods for protecting wounds, such as surgical incisions. In one embodiment, a dressing for protecting a wound includes: a support cushion configured to surround the wound, the support cushion having sidewalls defining a major axis and a minor axis, the support cushion including at least two perforations that traverse the sidewalls at offset locations; a reservoir configured to be suspended over and in engagement with the support cushion; and a cover configured to be positioned over the reservoir. The at least two perforations may define first and second interlocking J-shaped portions. The support cushion may include a wicking portion configured to surround the wound and a hydrophobic portion configured to surround the hydrophobic portion. The wicking portion may be configured to transfer fluid from the wound to the reservoir. Methods of applying the dressing, and kits including the dressing, also are provided.

24 Claims, 13 Drawing Sheets

U.S. PATENT DOCUMENTS

| | | | | |
|---|---|---|---|---|
| 5,060,662 A | | 10/1991 | Farnswoth, III | |
| 5,086,763 A | | 2/1992 | Hathman | |
| 5,086,764 A | * | 2/1992 | Gilman | 602/42 |
| 5,101,837 A | | 4/1992 | Perrin | |
| 5,106,362 A | * | 4/1992 | Gilman | 602/47 |
| 5,215,539 A | | 6/1993 | Schoolman | |
| 5,264,218 A | | 11/1993 | Rogozinski | |
| 5,356,372 A | | 10/1994 | Donovan et al. | |
| 5,376,067 A | | 12/1994 | Daneshvar | |
| 5,449,340 A | | 9/1995 | Tollini | |
| 5,456,660 A | | 10/1995 | Reich et al. | |
| 5,478,308 A | | 12/1995 | Cartmell et al. | |
| 5,512,041 A | | 4/1996 | Bogart | |
| 5,527,265 A | | 6/1996 | McKeel | |
| 5,533,962 A | | 7/1996 | Peterman et al. | |
| 5,603,946 A | | 2/1997 | Constantine | |
| 5,695,456 A | | 12/1997 | Cartmell et al. | |
| 5,702,356 A | | 12/1997 | Hathman | |
| 5,792,089 A | | 8/1998 | Penrose et al. | |
| 5,817,145 A | | 10/1998 | Augustine et al. | |
| 5,843,011 A | | 12/1998 | Lucas | |
| 5,885,237 A | | 3/1999 | Kadash et al. | |
| 5,891,074 A | | 4/1999 | Cesarczyk | |
| 5,899,871 A | | 5/1999 | Cartmell et al. | |
| 5,947,914 A | | 9/1999 | Augustine | |
| 5,954,680 A | | 9/1999 | Augustine | |
| 5,961,480 A | | 10/1999 | Augustine | |
| 5,964,721 A | | 10/1999 | Augustine | |
| 5,964,723 A | | 10/1999 | Augustine | |
| 5,986,163 A | | 11/1999 | Augustine | |
| 6,000,403 A | | 12/1999 | Cantwell | |
| 6,005,159 A | | 12/1999 | Spier | |
| 6,010,527 A | | 1/2000 | Augustine et al. | |
| 6,013,097 A | | 1/2000 | Augustine et al. | |
| 6,043,408 A | | 3/2000 | Geng | |
| 6,045,518 A | | 4/2000 | Augustine | |
| 6,071,254 A | | 6/2000 | Augustine et al. | |
| 6,071,304 A | | 6/2000 | Augustine et al. | |
| 6,080,189 A | | 6/2000 | Augustine et al. | |
| 6,093,160 A | | 7/2000 | Augustine et al. | |
| 6,095,992 A | | 8/2000 | Augustine | |
| 6,110,197 A | | 8/2000 | Augustine et al. | |
| 6,113,561 A | | 9/2000 | Augustine | |
| 6,143,945 A | | 11/2000 | Augustine et al. | |
| 6,168,800 B1 | | 1/2001 | Dobos et al. | |
| 6,211,426 B1 | | 4/2001 | Abrams | |
| 6,213,965 B1 | | 4/2001 | Augustine et al. | |
| 6,213,966 B1 | | 4/2001 | Augustine | |
| 6,217,535 B1 | | 4/2001 | Augustine | |
| 6,235,047 B1 | | 5/2001 | Augustine et al. | |
| 6,267,740 B1 | | 7/2001 | Augustine et al. | |
| 6,283,931 B1 | | 9/2001 | Augustine | |
| 6,293,917 B1 | | 9/2001 | Augustine et al. | |
| 6,320,093 B1 | | 11/2001 | Augustine et al. | |
| 6,323,386 B1 | | 11/2001 | Stapf et al. | |
| 6,406,448 B1 | | 6/2002 | Augustine | |
| 6,407,307 B1 | | 6/2002 | Augustine | |
| 6,419,651 B1 | | 7/2002 | Augustine | |
| 6,420,622 B1 | | 7/2002 | Johnston et al. | |
| 6,420,623 B2 | | 7/2002 | Augustine | |
| 6,423,018 B1 | | 7/2002 | Augustine | |
| 6,426,066 B1 | | 7/2002 | Najafi et al. | |
| 6,436,063 B1 | | 8/2002 | Augustine et al. | |
| 6,440,156 B1 | | 8/2002 | Augustine et al. | |
| 6,458,109 B1 | | 10/2002 | Henley et al. | |
| 6,465,708 B1 | | 10/2002 | Augustine | |
| 6,468,295 B2 | | 10/2002 | Augustine et al. | |
| 6,485,506 B2 | | 11/2002 | Augustine | |
| 6,528,697 B1 | | 3/2003 | Knutson et al. | |
| 6,569,189 B1 | | 5/2003 | Augustine et al. | |
| 6,570,050 B2 | | 5/2003 | Augustine et al. | |
| 6,573,420 B2 | | 6/2003 | Staph et al. | |
| 6,580,012 B1 | | 6/2003 | Augustine et al. | |
| 6,585,670 B2 | | 7/2003 | Augustine et al. | |
| 6,589,270 B2 | | 7/2003 | Augustine | |
| 6,605,051 B2 | | 8/2003 | Augustine | |
| 6,626,891 B2 | | 9/2003 | Ohmstede | |
| 6,641,601 B1 | | 11/2003 | Augustine et al. | |
| 6,653,520 B1 | | 11/2003 | Mouton | |
| 6,685,681 B2 | | 2/2004 | Lockwood et al. | |
| 6,716,235 B2 | | 4/2004 | Augustine et al. | |
| 6,840,915 B2 | | 1/2005 | Augustine | |
| 6,921,374 B2 | | 7/2005 | Augustine | |
| 6,960,181 B2 | | 11/2005 | Stevens | |
| 6,974,428 B2 | | 12/2005 | Knutson et al. | |
| 7,012,170 B1 | | 3/2006 | Tomaioulo | |
| 7,074,982 B2 | | 7/2006 | Knutson et al. | |
| 7,112,712 B1 | | 9/2006 | Ancell | |
| 7,118,545 B2 | | 10/2006 | Boyde | |
| 7,122,046 B2 | | 10/2006 | Augustine et al. | |
| 7,122,712 B2 | | 10/2006 | Lutri et al. | |
| 7,135,606 B1 | | 11/2006 | Dozier et al. | |
| 7,176,343 B2 | | 2/2007 | Schlussel | |
| 7,183,454 B1 | | 2/2007 | Rosenberg | |
| 7,276,051 B1 | | 10/2007 | Henley et al. | |
| 7,619,130 B2 | | 11/2009 | Nielsen et al. | |
| 7,695,444 B1 | * | 4/2010 | Simmons et al. | 602/79 |
| 8,067,662 B2 | * | 11/2011 | Aali et al. | 602/43 |
| 2001/0051781 A1 | | 12/2001 | Augustine et al. | |
| 2002/0007136 A1 | | 1/2002 | Narula et al. | |
| 2002/0026133 A1 | | 2/2002 | Augustine et al. | |
| 2002/0029010 A1 | | 3/2002 | Augustine et al. | |
| 2002/0138030 A1 | | 9/2002 | Cavanagh et al. | |
| 2003/0009122 A1 | | 1/2003 | Veras | |
| 2003/0036715 A1 | | 2/2003 | Knutson et al. | |
| 2003/0088201 A1 | | 5/2003 | Darcey | |
| 2004/0249328 A1 | | 12/2004 | Linnane et al. | |
| 2005/0004500 A1 | | 1/2005 | Rosser et al. | |
| 2005/0010153 A1 | | 1/2005 | Lockwood et al. | |
| 2005/0070835 A1 | | 3/2005 | Joshi | |
| 2005/0080372 A1 | | 4/2005 | Nielsen et al. | |
| 2005/0107732 A1 | | 5/2005 | Boyde | |
| 2005/0113731 A1 | | 5/2005 | Qvist | |
| 2005/0148921 A1 | | 7/2005 | Hsu | |
| 2005/0222528 A1 | | 10/2005 | Weston | |
| 2006/0064049 A1 | | 3/2006 | Marcussen | |
| 2006/0116620 A1 | | 6/2006 | Oyaski | |
| 2006/0189909 A1 | | 8/2006 | Hurley et al. | |
| 2006/0235347 A1 | * | 10/2006 | Aali | 602/41 |
| 2006/0253089 A1 | | 11/2006 | Lin | |
| 2007/0010778 A1 | * | 1/2007 | Burrell et al. | 602/54 |
| 2007/0041960 A1 | | 2/2007 | Freeman et al. | |
| 2007/0055205 A1 | | 3/2007 | Wright et al. | |
| 2007/0142757 A1 | | 6/2007 | Aali | |
| 2007/0142761 A1 | | 6/2007 | Aali | |
| 2007/0161937 A1 | | 7/2007 | Aali | |
| 2007/0161938 A1 | | 7/2007 | Aali | |
| 2007/0191754 A1 | | 8/2007 | Aali | |
| 2007/0212959 A1 | | 9/2007 | Johnson | |
| 2008/0091133 A1 | | 4/2008 | Matter | |

FOREIGN PATENT DOCUMENTS

| | | |
|---|---|---|
| DE | 731255 C | 2/1943 |
| DE | 1963375 A1 | 6/1971 |
| DE | 9302166 U1 | 7/1994 |
| DE | 29820217 U1 | 5/1999 |
| EP | 0117714 A2 | 9/1984 |
| EP | 1303239 B1 | 10/2007 |
| FR | 2583636 A1 | 12/1986 |
| WO | WO 85/01439 A1 | 4/1985 |
| WO | WO 96/15745 A1 | 5/1996 |
| WO | WO 98/53778 A1 | 12/1998 |
| WO | WO 00/07653 A1 | 2/2000 |
| WO | WO 01/49233 A1 | 7/2001 |
| WO | WO 01/93793 A1 | 12/2001 |
| WO | WO 02/05737 A1 | 1/2002 |
| WO | WO 2005/070480 | 8/2005 |
| WO | WO 2007/011596 A2 | 1/2007 |

OTHER PUBLICATIONS

USPTO Final Office Action for U.S. Appl. No. 11/409,364, 9 pages (mailed Mar. 10, 2009).
USPTO Non-Final Office Action for U.S. Appl. No. 11/409,364, 7 pages (mailed May 22, 2008).
USPTO Advisory Action for U.S. Appl. No. 11/409,364, 3 pages (mailed Apr. 8, 2008).

USPTO Final Office Action for U.S. Appl. No. 11/409,364, 7 pages (mailed Nov. 30, 2007).
USPTO Non-Final Office Action for U.S. Appl. No. 11/409,364, 7 pages (mailed May 31, 2007).
USPTO Examiner Interview Summary and Non-Final Office Action for U.S. Appl. No. 11/303,463, 9 pages (mailed Aug. 20, 2009).
USPTO Non-Final Office Action for U.S. Appl. No. 11/303,463, 10 pages (mailed Mar. 17, 2009).
USPTO Final Office Action for U.S. Appl. No. 11/303,463, 9 pages (mailed Dec. 26, 2008).
USPTO Non-Final Office Action for U.S. Appl. No 11/303,463, 11 pages (mailed Mar. 18, 2008).
USPTO Final Office Action for U.S. Appl. No. 11/107,452, 8 pages (mailed Dec. 24, 2009).
USPTO Non-Final Office Action for U.S. Appl. No. 11/107,452, 11 pages. (mailed Mar. 17, 2009).
USPTO Final Office Action for U.S. Appl. No. 11/107,452, 8 pages (mailed Sep. 19, 2008).
USPTO Non-Final Office Action for U.S. Appl. No. 11/107,452, 7 pages (mailed Dec. 4, 2007).
USPTO Non-Final Office Action for U.S. Appl. No. 11/107,452, 8 pages (mailed May 31, 2007).
USPTO Final Office Action for U.S. Appl. No. 11/707,464, 9 pages (mailed Dec. 24, 2009).
USPTO Non-Final Office Action for U.S. Appl. No. 11/707,464, 11 pages (mailed Apr. 14, 2009).
USPTO Non-Final Office Action for U.S. Appl. No. 11/707,464, 8 pages (mailed Jun. 27, 2008).
USPTO Notice of Allowance for U.S. Appl. No. 11/303,155, 5 pages (mailed Jun. 12, 2009).
USPTO Non-Final Office Action for U.S. Appl. No. 11/303,155, 7 pages (mailed Jan. 8, 2009).
USPTO Non-Final Office Action for U.S. Appl. No. 11/303,155, 9 pages (mailed Jul. 14, 2008).
USPTO Non-Final Office Action for U.S. Appl. No. 11/441,702, 7 pages (mailed Oct. 27, 2009).
USPTO Final Office Action for U.S. Appl. No. 11/441,702, 12 pages (mailed Apr. 10, 2009).
USPTO Non-Final Office Action for U.S. Appl. No. 11/441,702, 8 pages (mailed Jun. 26, 2008).
USPTO Non-Final Office Action for U.S. Appl. No. 11/441,702, 9 pages (mailed May 1, 2007).
Written Opinion of the International Searching Authority for PCT/US2010/028785, 7 pages (mailed Aug. 6, 2010).
International Search Report for PCT/US2010/028785, 5 pages (mailed Aug. 6, 2010).
Written Opinion of the International Searching Authority for PCT/US2010/037196, 10 pages (mailed Nov. 3, 2010).
International Search Report for PCT/US2010/037196, 6 pages (mailed Nov. 3, 2010).
USPTO Final Office Action for U.S. Appl. No. 11/303,463, 10 pages (mailed Apr. 8, 2010).
USPTO Notice of Allowance for U.S. Appl. No. 11/107,452, 5 pages (mailed Apr. 29, 2010).
USPTO Notice of Allowance for U.S. Appl. No. 11/707,464, 5 pages (Mailed Sep. 3, 2010).
USPTO Non-Final Office Action for U.S. Appl. No. 11/707,464, 9 pages (mailed Apr. 14, 2010).
USPTO Notice of Allowance for U.S. Appl. No. 11/441,702, 4 pages (mailed Apr. 12, 2010).
USPTO Notice of Allowance for U.S. Appl. No. 12/416,826, 8 pages (mailed Oct. 7, 2011).
USPTO Non-Final Office Action for U.S. Appl. No. 12/416,826, 16 pages (mailed May 24, 2011).

* cited by examiner

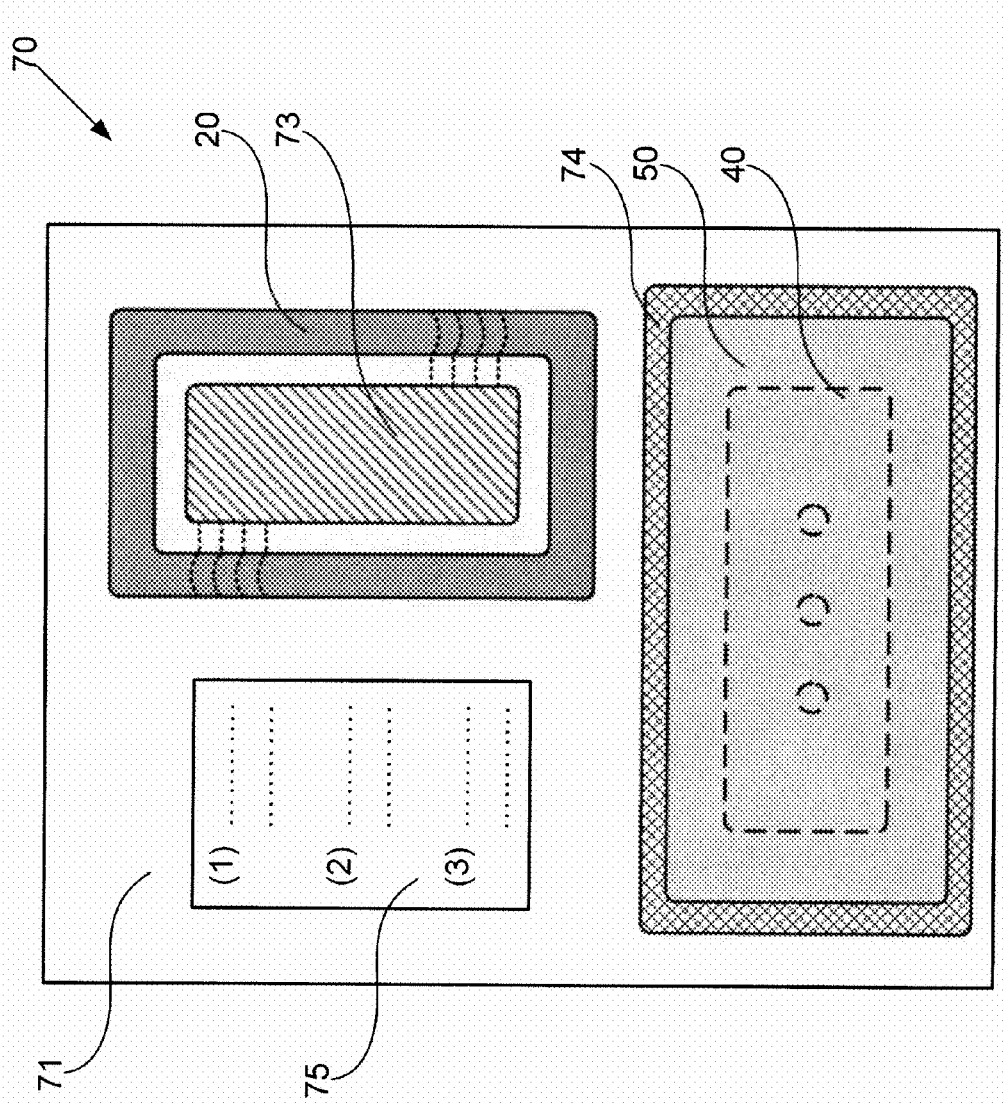

SYSTEMS AND METHODS FOR PROTECTING INCISIONS

I. FIELD OF THE INVENTION

This application generally relates to systems and methods for protecting wounds, particularly incisions.

II. BACKGROUND OF THE INVENTION

Wounds occur when the integrity of tissue is compromised, affecting one or more layers of the epidermis or underlying tissue. There are several types of wounds, including acute, chronic, and iatrogenic wounds. Acute wounds may be caused by an initiating event, such as a accident-related injury, surgical procedure or by operation of an infectious disease. Acute wounds caused by accident-related injuries generally take the form of punctures, abrasions, cuts, lacerations, or burns. Acute wounds caused by surgical procedures may be in the form of incisions caused by cutting into or through the skin using a scalpel or other sharp instrument. For example, depending on the procedure, an incision may extend through some or all of the layers of the skin, e.g., through the epidermis, dermis and subcutis, as well as into or through muscle, bone, ligaments, and/or internal organs as needed for the surgeon to be able to access the body part to be treated. Chronic wounds are wounds that generally do not heal within three months, due to one or more of ischemia of the vessels supplying the tissue, venous hypertension or compromise of the immune response, such as observed, for example, with venous ulcers, diabetic ulcers and pressure ulcers. Depending on etiology, such as diabetes, venous insufficiency, or cardiovascular failures, acute wounds may become recalcitrant and even chronic. Iatrogenic wounds are wounds that were initially acute and caused by surgical incision, but become infected.

There are three general classes of wound treatment techniques, commonly referred to as "primary intention," "secondary intention," and "tertiary intention." Primary intention may be used to treat acute wounds that are clean, uninfected, and involve little tissue loss, such as surgical incisions. In a primary intention technique, the edges of the wound are brought together and secured, e.g., using sutures, staples, or adhesive strips. Such wounds have a relatively low risk of infection.

Secondary intention may be used to treat acute or chronic wounds in which there may be sufficient loss of tissue and/or of structural integrity, which may have been caused by tissue necrosis or excision, that primary intention would be inappropriate, e.g., that the skin would need to be stretched too far to safely close the wound with sutures or adhesive. In a secondary intention technique, the wound is left open and allowed to close on its own by the reparative process. Exudate may be allowed to drain freely, and granulation tissue allowed to fill the cavity of the wound. Such wounds have a relatively high risk of infection because they may be exposed to the environment and may be slow to heal.

Tertiary intention, which is sometimes also referred to as "delayed primary closure," may be appropriate to treat acute wounds that are infected or otherwise experiencing complications, e.g., iatrogenic wounds. In a tertiary intention technique, the wound is often left open for a period of time to allow the complication to at least partially resolve, and then closed using primary intention, e.g., sutures, staples, or adhesive. For example, temporarily leaving such a wound open may allow edema (swelling) or infection to resolve, exudate to drain from the wound, the wound edges to contract, and/or granulation tissue to form. Such wounds may be associated with a high risk of infection and a large loss of tissue.

Conventional wound treatment also typically involves covering the wound with a dressing to prevent further contamination and infection, to retain moisture, and to absorb fluids such as blood or exudate. While exudate contains biochemical compounds that benefit wound healing, excessive exudate in the wound or in the region surrounding the wound, called the "periwound region," may facilitate degradation of tissue and/or serve as a growth medium for bacteria. For patients with acute wounds and otherwise healthy skin, the presence of excess fluid such as exudate is not a significant concern. However, for patients with chronic wounds, the presence of excess fluid, particularly excess exudate, may delay healing and further damage the skin in the periwound region.

Conventional wound dressings also typically do not address the pain created by the wound treatment system, particularly where the wound treatment system continuously contacts the wound. For example, gauze, which is applied directly onto a wound, is capable of absorbing only a limited amount of exudate, and readily transports excess exudate onto the periwound region, which may cause maceration and damage. Moreover, gauze typically is placed in direct contact with, and adheres to the wound bed, so that normal motion of the patient results in rubbing, itching and discomfort. In addition, removal of the gauze at periodic intervals may be painful and may disrupt at least some of the healing that may have occurred.

Wounds covered with conventional dressings, such as gauze, are also vulnerable to "dehiscence," or unintentional reopening of the wound. Dehiscence may be caused by physical trauma to the wound and/or by poor wound healing. For example, an incision treated using primary intention, e.g., that is sutured and covered with gauze, may inadvertently be opened if skin on one side of the incision is pulled away from skin on the other side of the incision. Although the sutures may resist such lateral forces, the wound may at least partially open, disrupting some of the healing that may have occurred. The skin may also tear in the vicinity of the sutures, depending on the magnitude of the force. Wounds treated by secondary or tertiary intention may be at least as vulnerable to dehiscence as those treated by primary intention, because they not only lack sutures for resisting such lateral forces, but also may have worse structural integrity because of poor skin health in the region of the wound. Poor wound healing also can increase the risk of dehiscence. For example, patients with poor circulation, e.g., diabetics, may have low blood supply in certain parts of their body which may delay wound healing. Some patients may have genetic disorders, diseases, or may take medications that suppress the formation of collagen and/or other tissues needed for healing. Additionally, the longer it takes a wound to heal, the longer the time over which the wound is vulnerable to reopening by physical trauma, which can further delay healing.

Conventional dressings, such as gauze, do not adequately resist lateral physical forces that may cause wound dehiscence, and do not adequately manage fluid that may drain from the wound, among other shortcomings. For example, U.S. Pat. No. 5,060,662 to Farnsworth discloses a bandage including a ring of pliant material, such as a flexible foam, which is disclosed as holding the rest of the bandage out of contact with the wound. Farnsworth discloses that the bandage further includes an air permeable member, fabricated of a material such as nylon gauze, which is affixed to the upper side of the ring; and an outer protective layer, having a plurality of relatively large openings, which is affixed to the air permeable member. Although Farnsworth discloses that the ring, air permeable layer, and protective layer are formed with lines of perforations permitting the bandage to be separated into sections for application to wounds of different sizes, the separate pieces do not interlock with one another when applied around the wound. The separate pieces are therefore susceptible to being separated by lateral forces and, as such, would not adequately resist those lateral forces to protect the wound from dehiscence.

U.S. Pat. No. 6,570,050 to Augustine et al. discloses a bandage for autolytic wound debridement that includes a fluid-impermeable enclosure including a fluid-absorbent material that is positioned to receive and retain exuded fluid that originates in the wound. Augustine discloses that when the enclosure is attached to the skin it creates a closed chamber over the wound, that maintains a near-100% humid atmosphere about the wound. Augustine teaches that such high humidity is desirable, but failed to recognize that collecting exuded fluid in such a chamber may macerate and damage the skin under the chamber. Moreover, the fluid-impermeable enclosure may create a ring of pressure where it contacts the skin, which may not only damage that skin but may actually enhance dehiscence of the wound. Additionally, the bandage of Augustine is not adjustable, and so can only be used with wounds having a narrow range of sizes.

U.S. Pat. No. 7,193,454 to Rosenberg discloses an occlusive dressing system that includes an endless, elongated, flexible, adhesive barrier adapted to be arranged around a wound, and an impermeable sealing film adapted to overlie the barrier and to seal the wound from the environment. Like Augustine, Rosenberg failed to recognize that such a sealed environment may macerate and damage the skin. Additionally, the flexible barrier would provide little resistance to lateral forces, and thus little protection against wound dehiscence, and the impermeable sealing film would not cushion the wound against forces applied from above the wound.

Thus, what is needed is a dressing that resists lateral physical forces that may cause wound dehiscence, that cushions the wound, and manages fluid that may drain from the wound, among other shortcomings.

III. SUMMARY OF THE INVENTION

The present invention provides systems and methods for protecting wounds such as incisions by resisting lateral forces that may cause dehiscence, by cushioning the wounds from external pressure sources, and absorbing exudate or other fluids from the wounds. The dressings of the present invention may be used to protect a wide range of acute, chronic, and infected wounds, including surgical incisions. For example, dressings constructed in accordance with the present invention may be advantageously used to protect surgical areas where skin is most vulnerable, such as split-thickness graft sites and cosmetic surgeries.

Dressings constructed in accordance with the present invention also may advantageously be used to protect acute wounds from further trauma, such as may occur in industrial accidents and in the battle field settings. In particular, dressings in accordance with the present invention may be applied to reduce contact pressure on the wound bed. In a battlefield setting, for example, this aspect of the invention may be particularly valuable, since a bandaged wound may still have debris or shrapnel in it, and the dressing can be applied to prevent such contaminants from being pushed further into the wound during evacuation of the wounded subject.

In accordance with one aspect of the present invention, a dressing for protecting a wound includes: a support cushion configured to surround the wound, the support cushion having sidewalls defining a major axis and a minor axis, the support cushion including at least two perforations that traverse the sidewalls at offset locations; a reservoir configured to be suspended over and in engagement with the support cushion; and a cover configured to be positioned over the reservoir.

The at least two perforations may define first and second interlocking J-shaped portions. The support cushion may comprise a hydrophobic portion and a wicking portion, the wicking portion being configured to surround the wound and the hydrophobic portion being configured to surround the wicking portion. The wicking portion may be configured to transfer fluid from the wound to the reservoir. The cover may be configured to retain the reservoir in engagement with the wicking portion. The wicking portion may define a flange of the support cushion, the flange having a ledge to accept a portion of the reservoir.

The support cushion may include additional perforations that enable removal of selected portions of the support cushion along the major axis to reduce a length of the support cushion along the major axis. The support cushion may include additional perforations that enable removal of selected portions of the support cushion along the minor axis to reduce a width of the support cushion along the minor axis. At least a portion of each of the at least two perforations is curved. There may be a plurality of perforations defined in the reservoir to enable removal of selected portions of the reservoir. The support cushion may further comprise a hydrophobic barrier. The dressing may further comprise a biocompatible adhesive for securing the support cushion around the wound. The reservoir may comprise a first hydrophilic layer, a non-stretchable mesh or scrim, and a second hydrophilic layer. The cover may comprise a breathable material. A vent may be defined in the reservoir, the vent permitting humidity over the wound to escape through the cover. A biocompatible adhesive may secure the cover to the reservoir. A biocompatible adhesive may secure the cover to the support cushion. Some embodiments include means for repeatedly attaching and detaching the cover to the support cushion so that the wound is viewable without entirely removing the dressing.

Under another aspect, a method for protecting a wound includes: providing a support cushion configured to surround the wound, the support cushion having sidewalls defining a major axis and a minor axis, the support cushion including at least two perforations that traverse the sidewalls at offset locations; surrounding the wound with a support cushion; applying a reservoir over the support cushion; and transferring fluid from the wound to the reservoir.

In some embodiments, a plurality of additional perforations may be defined in the support cushion, the method further comprising reducing a size of the support cushion along the major axis by removing selected portions of the support cushion. The reservoir may include a plurality of perforations, the method further comprising reducing a size of the reservoir by removing a selected portion of the reservoir along at least one perforation of the plurality of perforations defined in the reservoir. The support cushion may include a stepped profile that defines a ledge and a recess, the method further comprising fitting the reservoir within the recess so that the reservoir engages the ledge and is suspended over the wound. The support cushion may comprise a hydrophobic portion that defines the recess and a hydrophilic portion that defines the ledge. The method may further include securing a cover to the support cushion with a biocompatible adhesive.

Under another aspect, a kit for a dressing for use in protecting a wound includes: a support cushion configured to surround the wound, the support cushion having sidewalls defining a major axis and a minor axis, the support cushion including at least two perforations that traverse the sidewalls at offset locations; a reservoir configured to be applied over the support cushion; a backing upon which the support cushion and reservoir are mounted; and instructions for use printed on the backing, the instructions for use describing steps for assembling the dressing.

IV. BRIEF DESCRIPTION OF THE DRAWINGS

Figure 1A:
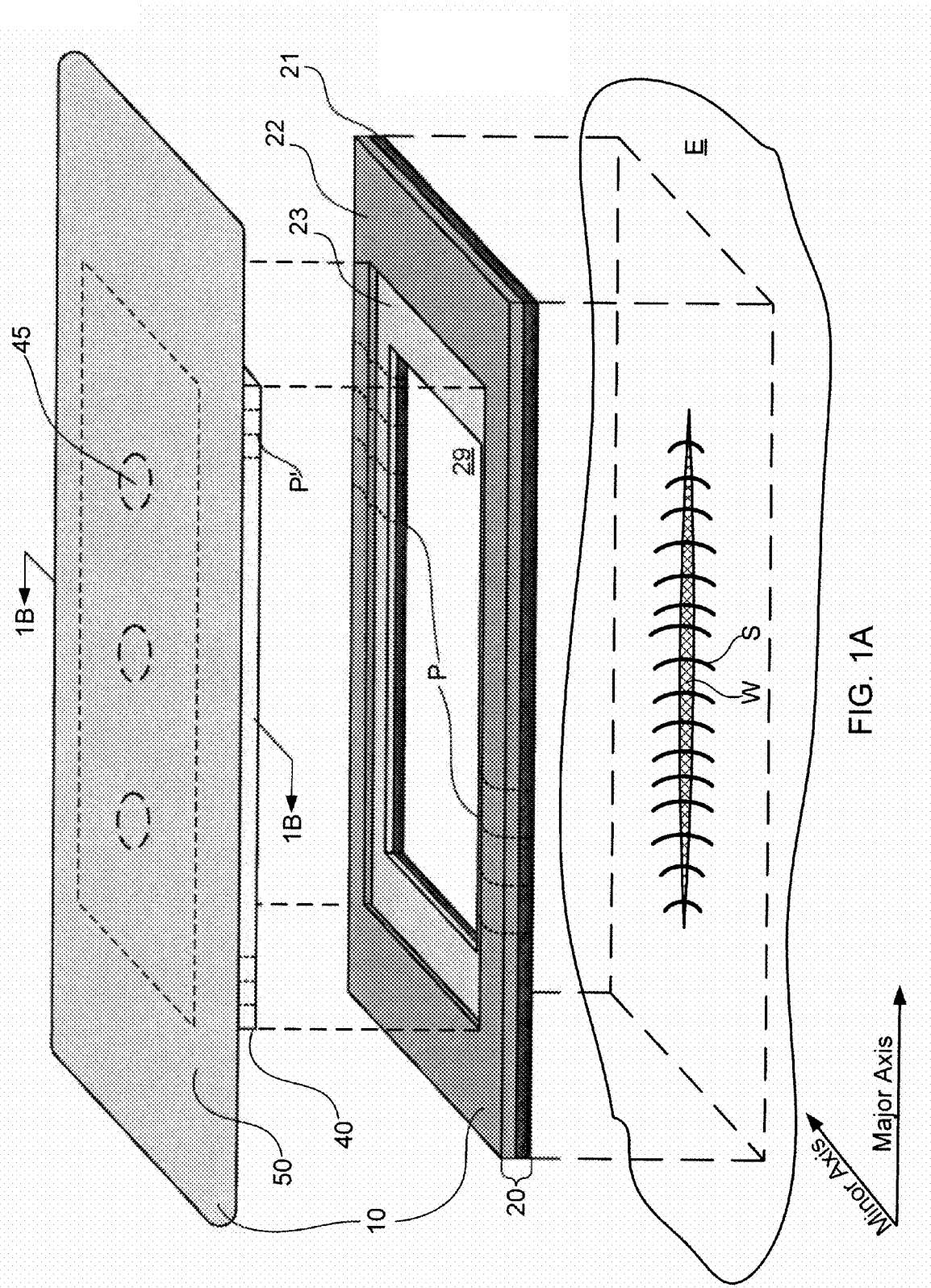
FIGS. 1A and 1B are an exploded view and a cross-sectional view, respectively, of an exemplary dressing of the present invention.
Figure 1B:
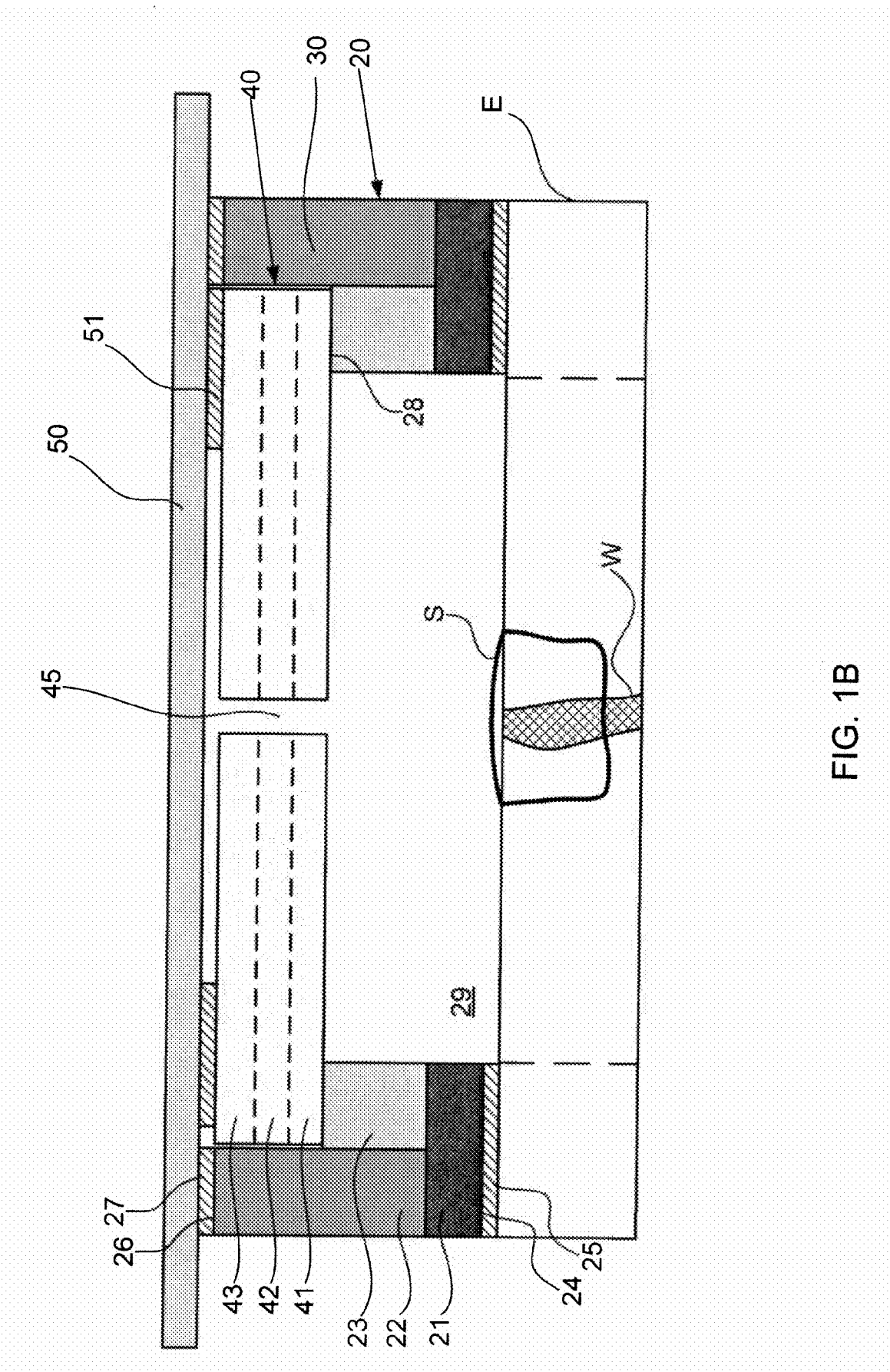
Figure 3A:
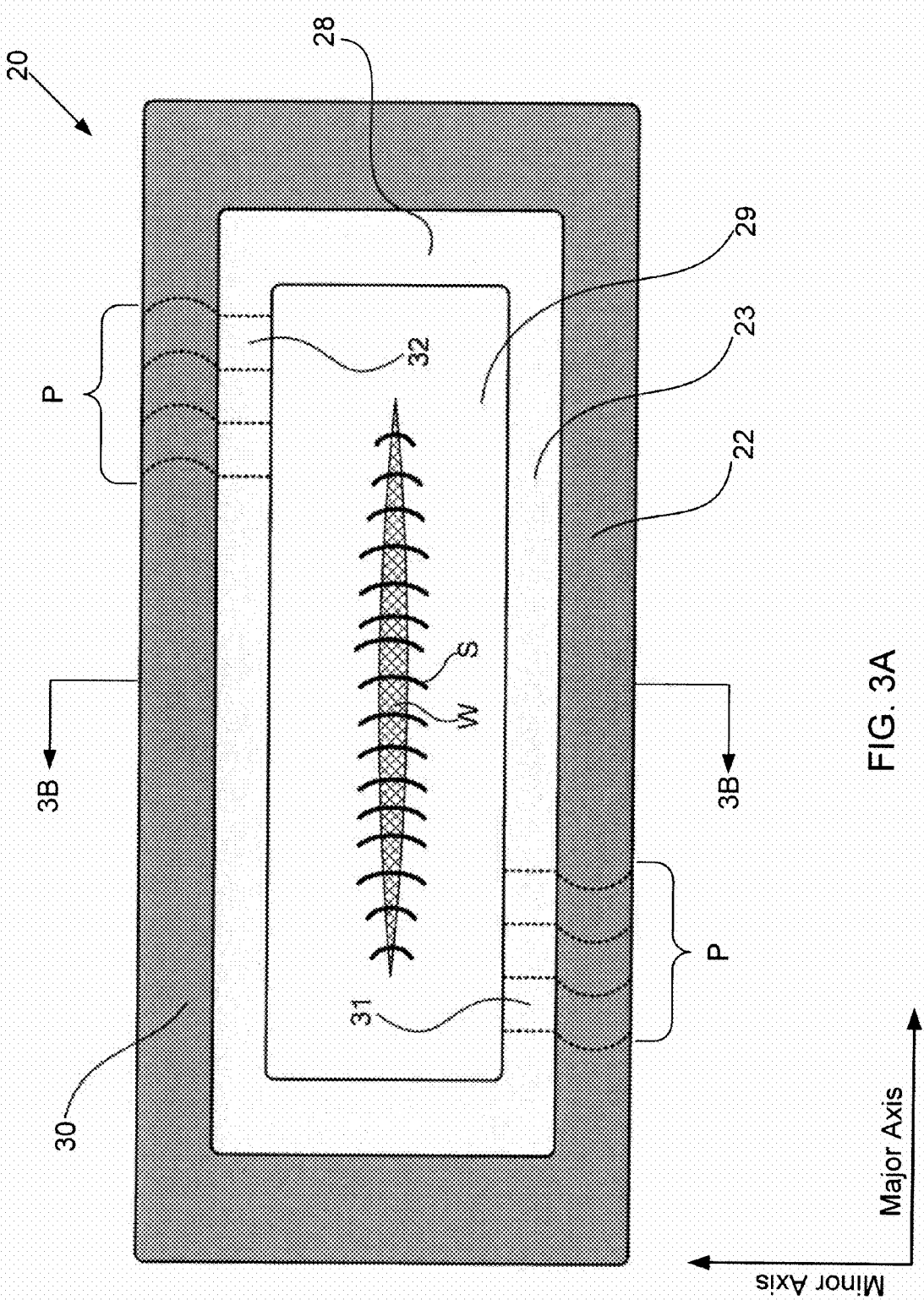

FIG. 3A schematically illustrates a plan view of the embodiment of the support cushion illustrated in FIGS. 1A-1B.

Figure 3B:
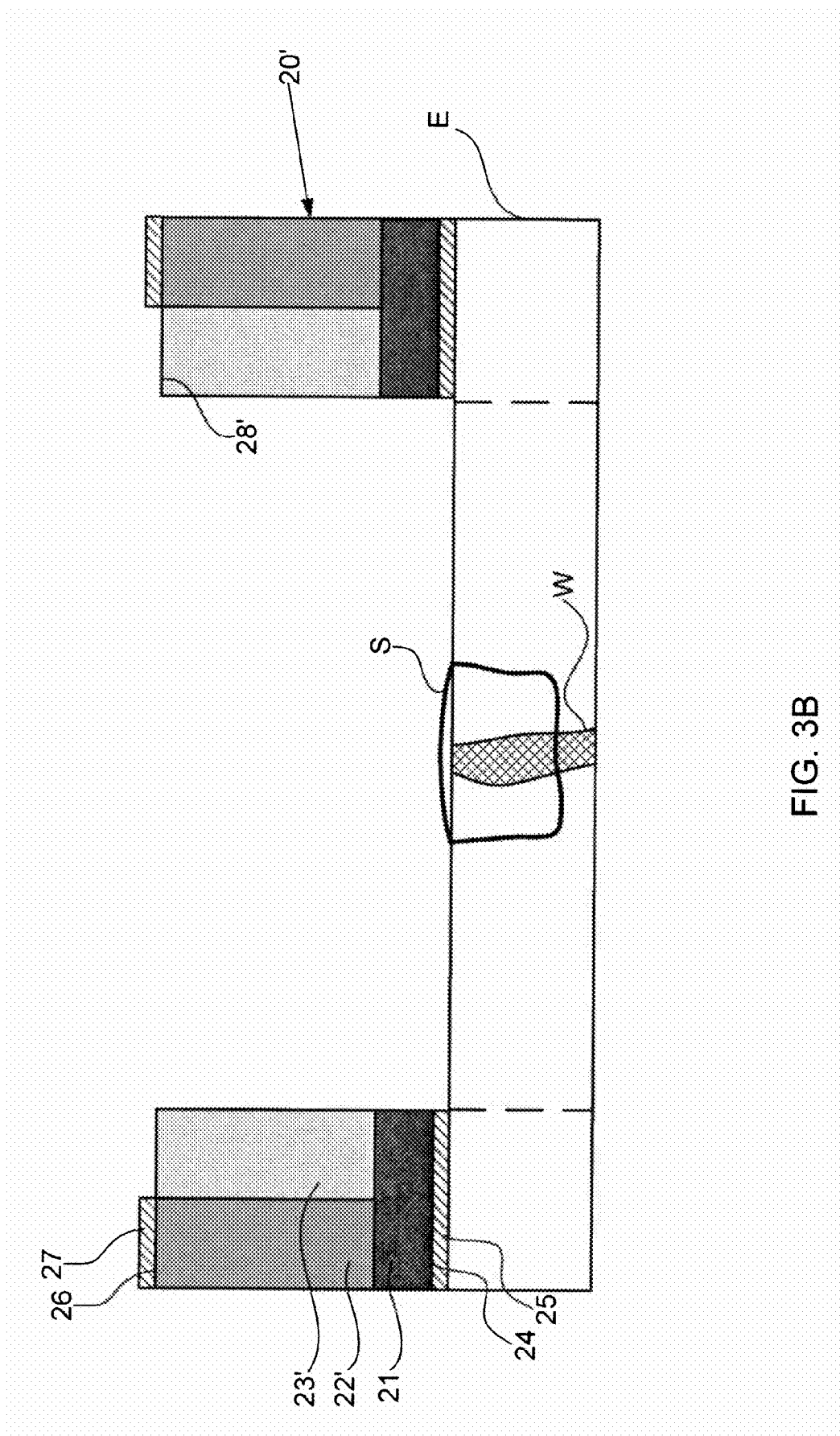

FIG. 3B schematically illustrates a cross-sectional view of an alternative embodiment of the support cushion.

Figure 3C:
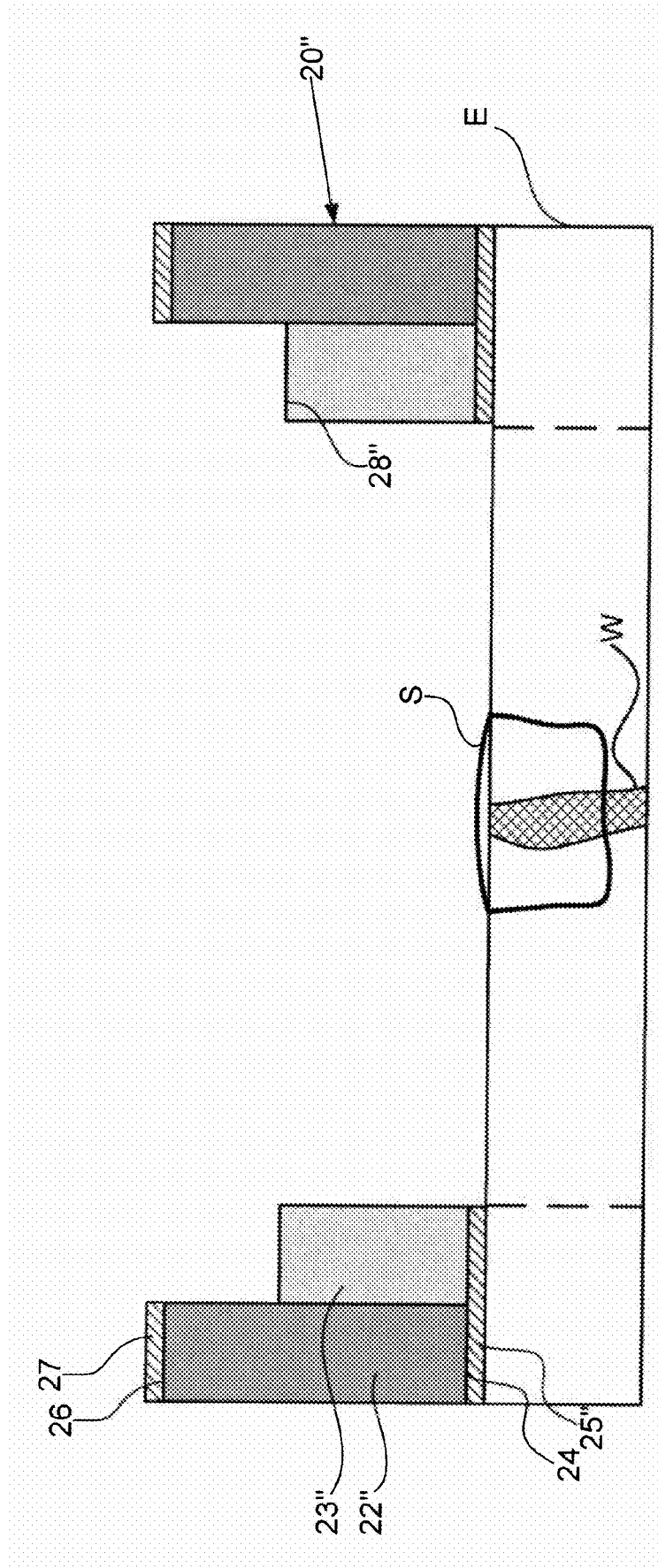

FIG. 3C schematically illustrates a cross-sectional view of another alternative embodiment of the support cushion.

Figure 3D:
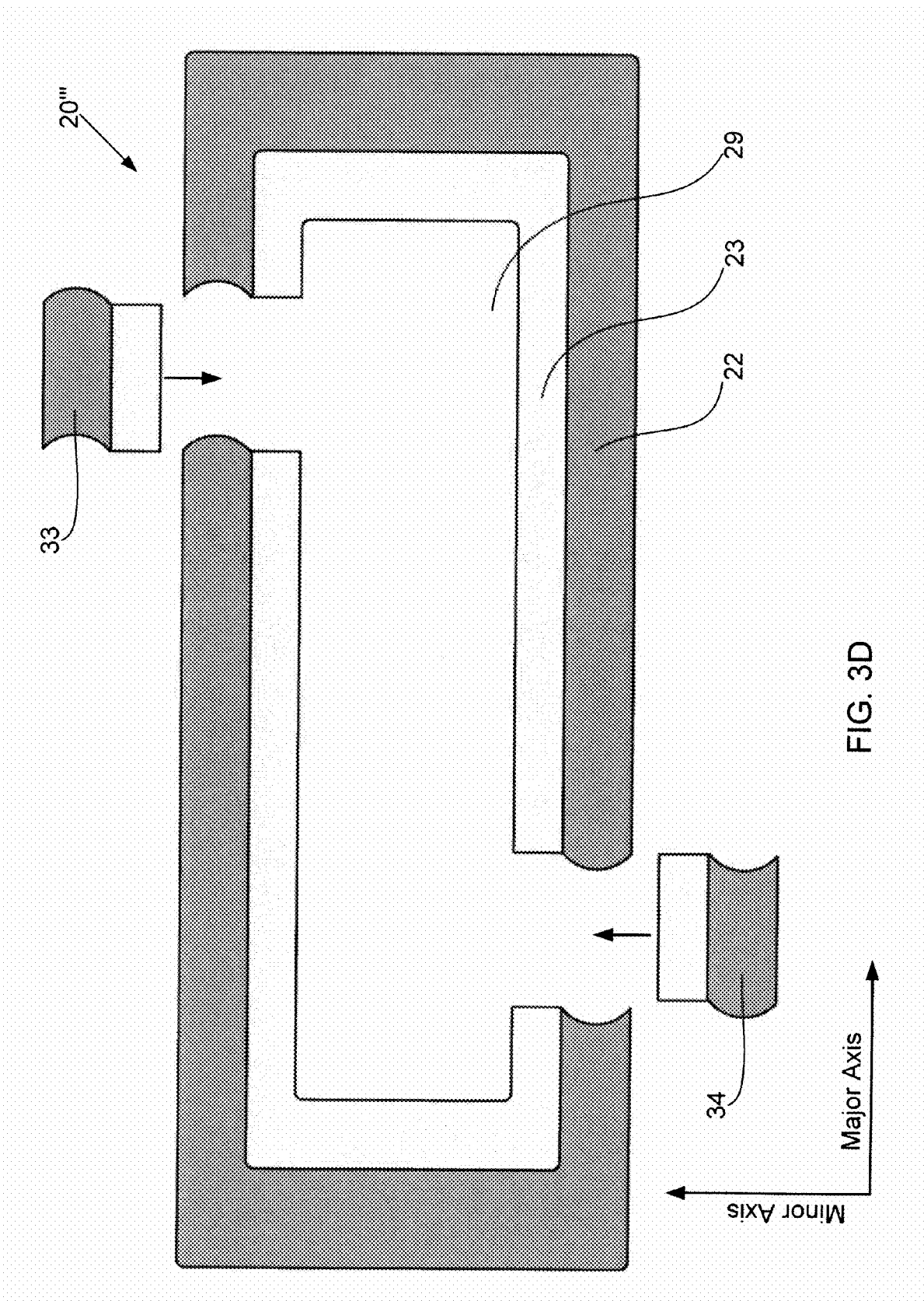

FIG. 3D schematically illustrates a plan view of another alternative embodiment of the support cushion.

Figure 4:
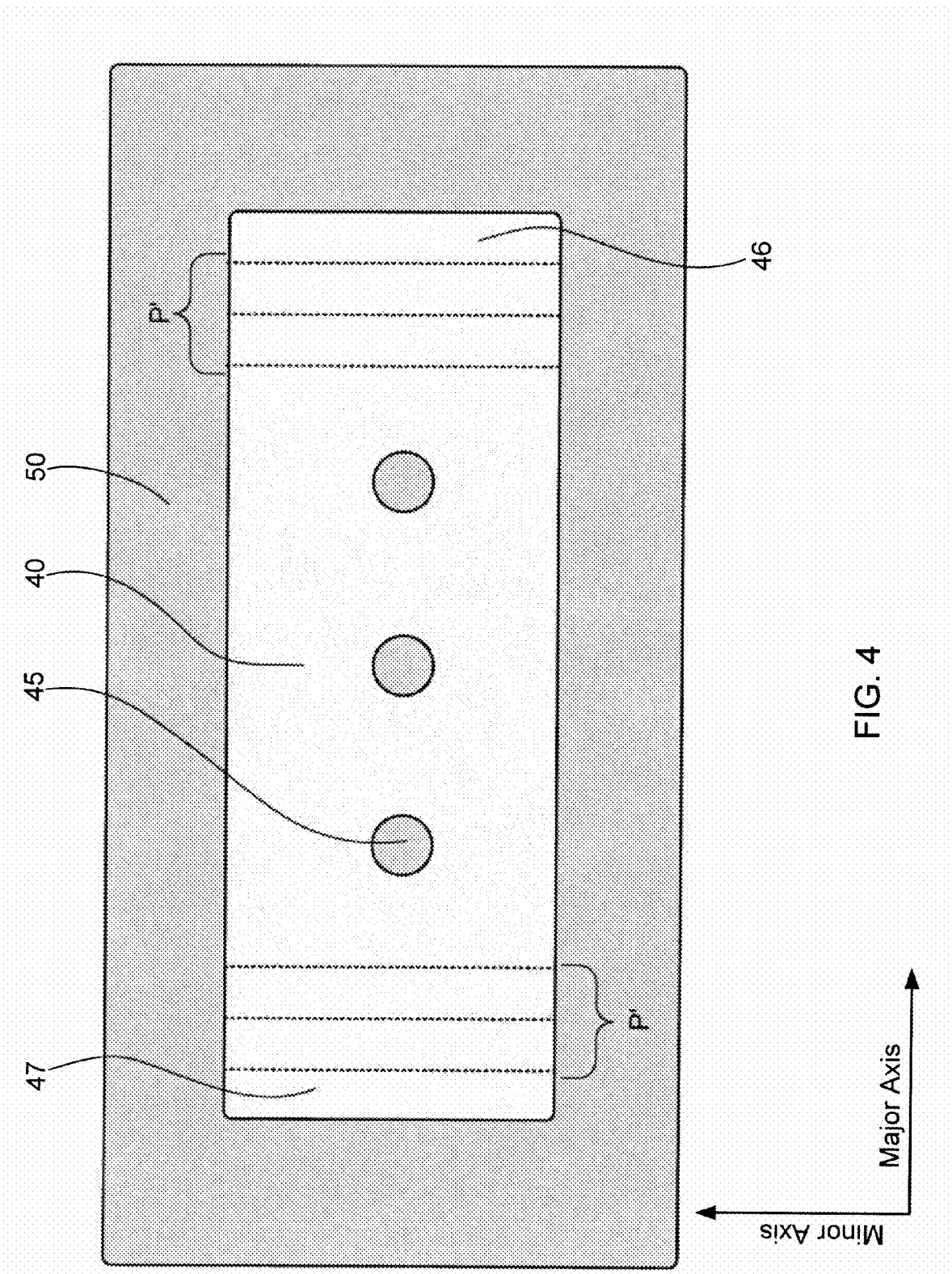

FIG. 4 schematically illustrates a plan view of a reservoir, cover, and optional vent according to some embodiments of the invention.

FIG. 5A schematically illustrates a plan view of a kit containing a system for incision protection, according to some embodiments of the invention.

Figure 5B:
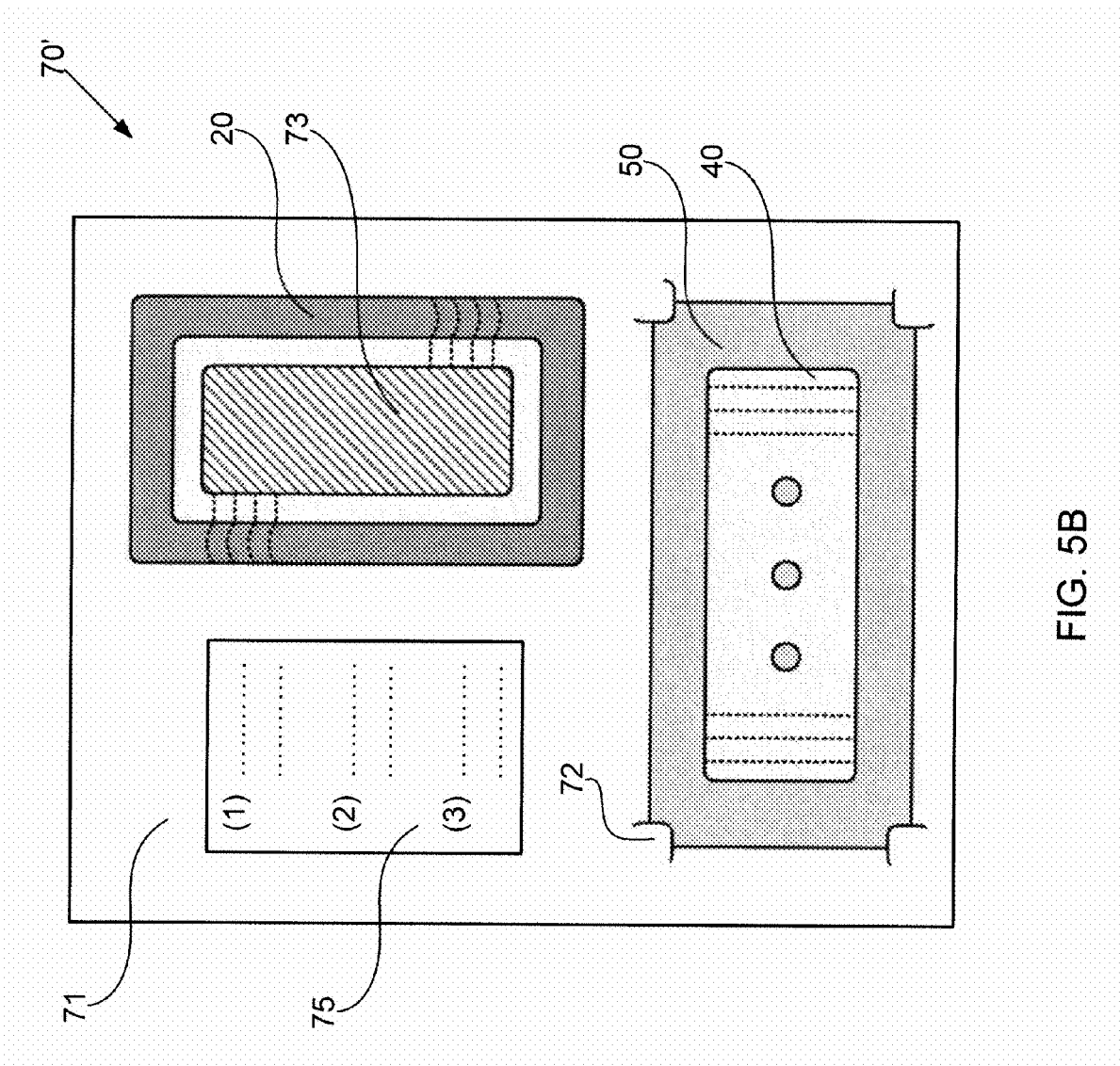

FIG. 5B schematically illustrates a plan view of an alternative kit containing a system for incision protection, according to some embodiments of the invention.

Figure 6A:
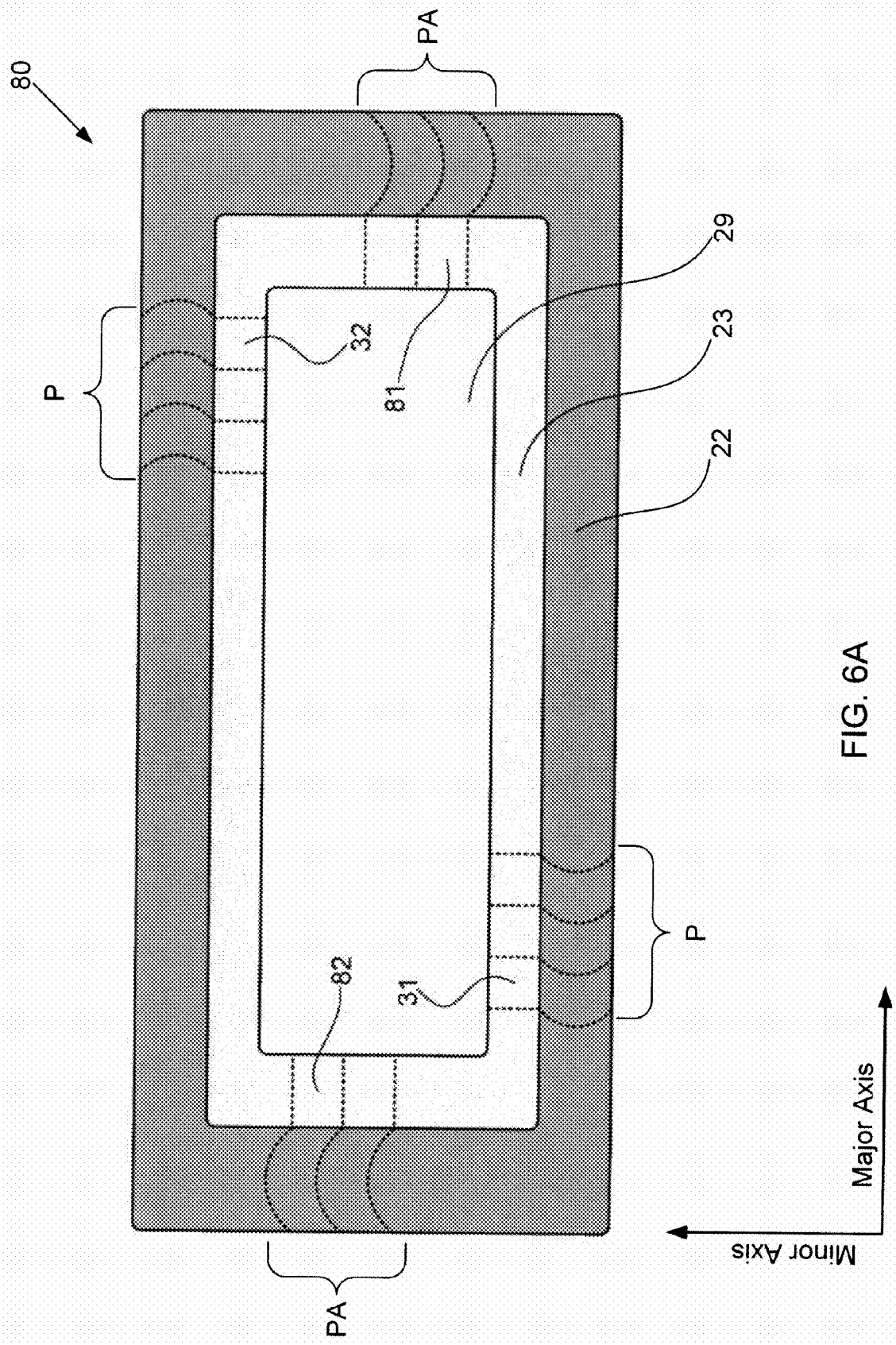

FIG. 6A schematically illustrates a plan view of another alternative embodiment of the support cushion.

Figure 6B:
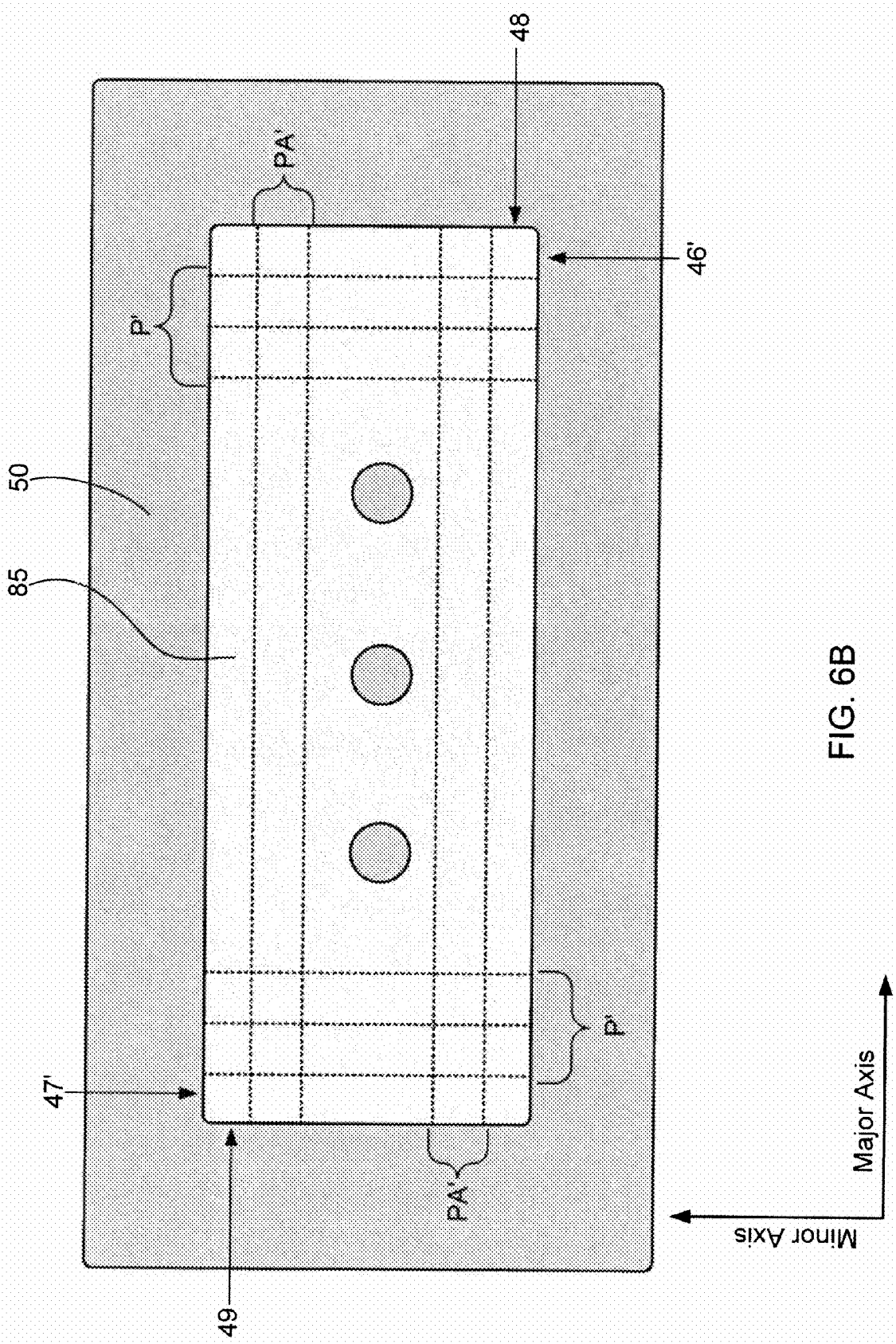

FIG. 6B schematically illustrates a plan view of an alternative embodiment of a reservoir, cover, and optional vent, according to some embodiments of the invention.

Figure 7:
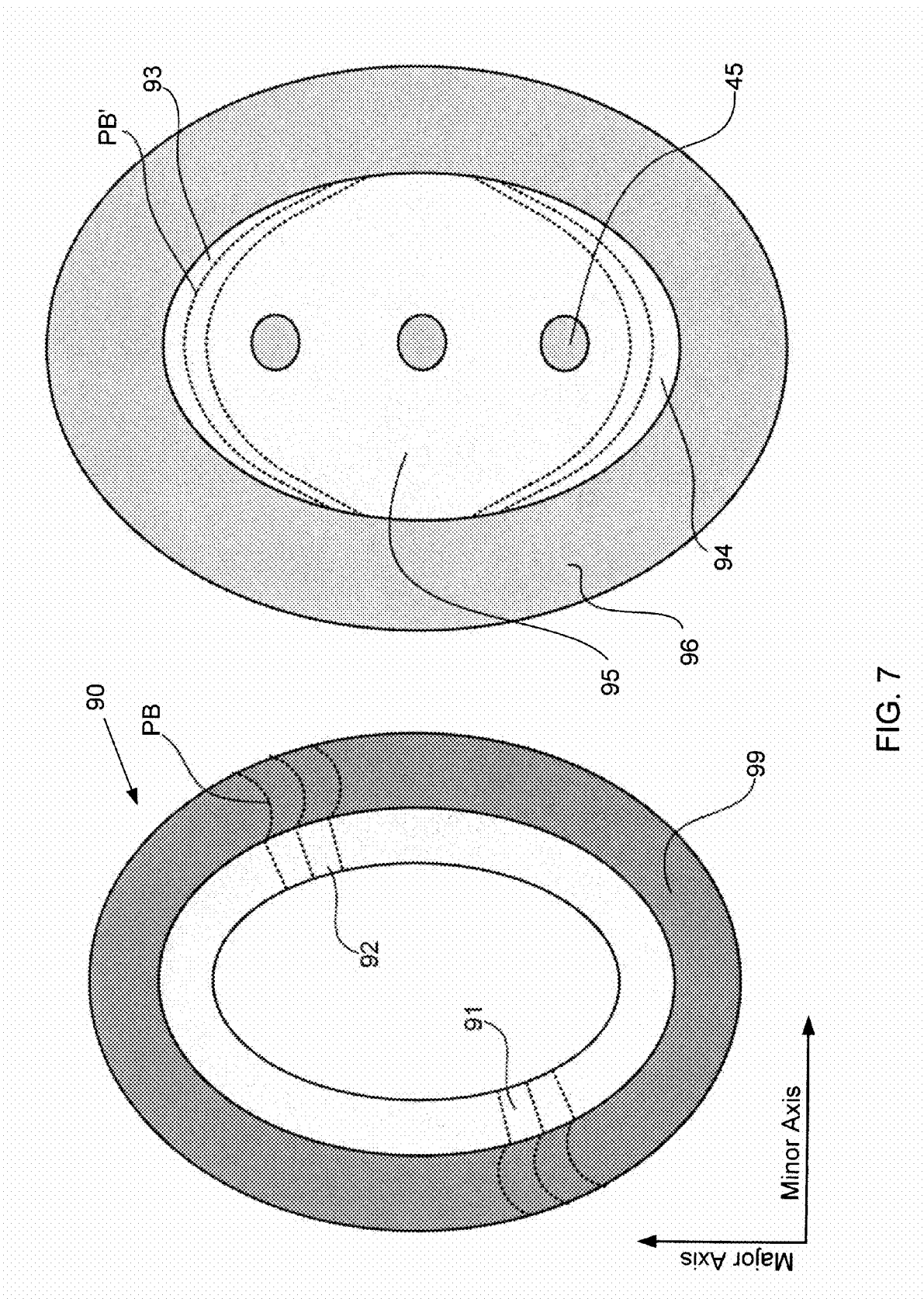

FIG. 7 schematically illustrates a plan view of yet another alternative embodiment of a support cushion and a reservoir, cover, and optional vent for use with that support cushion, according to some embodiments of the invention.

V. DETAILED DESCRIPTION OF THE INVENTION

The present invention provides systems and methods for protecting wounds, such as incisions. Among other things, the systems and methods provide a wound dressing that cushions the wound and also resists lateral forces, thus reducing the risk of wound dehiscence, particularly for wounds being treated using primary or tertiary intention. The dressing further transfers fluid away from the wound and into a reservoir that is suspended over, and not in continuous contact with, the wound. This arrangement promotes wound healing by reducing the disruption of the wound bed (and pain) caused by dehiscence and/or by periodic replacement of conventional dressings, such as gauze, which adhere to the wound bed.

An overview of an exemplary embodiment of a system for wound protection constructed in accordance with the principles of the present invention is first described, as well as a method of applying and using that system. Further details on the individual components employed in the system of the present invention, and alternative embodiments and methods, are described.

Overview of System

Referring now to FIGS. 1A and 1B, an exemplary embodiment of wound dressing 10, constructed in accordance with the principles of the present invention to provide wound protection, is described. In this exemplary embodiment, dressing 10 comprises two discrete components that are assembled and applied by the patient, nurse, clinician or other caregiver over wound W in patient's epidermis E. In the illustrated embodiment, wound W is secured closed using sutures S; that is, wound W is being treated with primary intention. However, it should be understood that the dressing can be applied to any type of wound, e.g., a wound being treated with primary, secondary, or tertiary intention.

Dressing 10 includes support cushion 20 and reservoir 40, which is preferably pre-attached to cover 50. Preferably, components 20, 40 and 50 of dressing 10 are sized for use with one another and are enclosed in a sterile package with suitable instructions to enable the patient or caregiver to quickly and accurately apply the dressing. Alternatively, because for some embodiments certain components of dressing 10, such as reservoir 40, may be replaced on a frequent basis than other portions of the dressing, such components may be individually packaged.

Support cushion 20 is designed to surround wound W and a surrounding region of epidermis E extending from the wound margin, to protect the wound and elevate reservoir 40 and cover 50 above the wound bed. In the exemplary embodiment of FIGS. 1A-1B, support cushion 20 includes sidewalls 30 defining a major axis and a minor axis. Additionally, as described in greater detail below, support cushion 20 and/or reservoir 40 are optionally constructed to include perforations P, P' enabling the sizes of these components to be adjusted to provide a better fit around a particular wound. For example, support cushion 20 optionally includes at least two perforations P that traverse the sidewalls 30 at offset locations. The perforations P defined in support cushion 20 may define first and second interlocking J-shaped portions of the sidewalls 30, and additionally may enable removal of selected portions of the support cushion along the major axis to reduce a length of the support cushion 20 along the major axis. Similarly, the perforations P' defined in reservoir 40 may enable removal of selected portions of the reservoir along the major axis to reduce a length of the reservoir along the major axis. Other possible configurations for the support cushion 20, reservoir 40, and perforations P, P' are provided further below.

In the illustrated embodiment, hydrophobic portion 22, which is preferably formed from a hydrophobic closed cell polyolefin foam, defines sidewalls 30. Support cushion may also include a wicking portion 23, preferably formed from a hydrophilic open-cell polyurethane foam. The wicking portion 23 may be configured to surround the wound W and the hydrophobic portion 22 may be configured to surround the wicking portion 23. The wicking portion 23 defines a flange, the upper surface 28 of which includes a ledge that accepts a portion of reservoir 40 and thereby supports reservoir 40, as depicted in FIG. 1B. Additionally, in the illustrated embodiment, support cushion 20 includes a hydrophobic barrier 21, preferably formed from a closed-cell polyurethane foam, under the hydrophobic portion 22 and the wicking portion 23. Hydrophobic barrier 21 inhibits seepage of fluid out of the support cushion 20 onto epidermis E. Lower surface 24 of support cushion 20 includes layer 25 of biocompatible adhesive, which preferably is hydrophobic and breathable, to secure the support cushion 20 to the epidermis E. Upper surface 26 of support cushion includes layer 27 of adhesive or a portion of a reusable fastening system, e.g., the pile of a hook and pile fastening system, such as Velcro, to secure cover 50 to the upper surface 26 of support cushion 20. Use of a non-permanent adhesive or a reusable fastening system for layer 27 permits the cover 50 to be periodically removed to inspect the wound, to apply topical medications or other substances to the wound, e.g., moisturizing ointments, growth factors, nutrients, and/or antibiotics, or to replace reservoir 40. In other embodiments, cover 50 and/or reservoir 40 are left in place over the wound while dressing 10 is applied to the patient. Support cushion 20 includes opening 29 that exposes a portion of the epidermis E surrounding wound W.

Still referring to FIG. 1, reservoir 40 preferably includes a sandwich of different density open cell polyurethane foams 41 and 43 joined to mesh or scrim 42, in which the foams 41 and 43 are selected to absorb fluid from wicking portion 23 and to sequester the fluid away from the wound bed. In the embodiment depicted in FIG. 1, reservoir 40 is fastened to the underside of cover 50, and is sized so that the outer edges of the reservoir are supported on ledge 28 of wicking portion 23, while the more central regions of the reservoir are suspended over the wound W and surrounding epidermis, thus inhibiting contact between reservoir 40 and wound W and limiting the extent to which force applied to cover 50 and reservoir 40 is transmitted to wicking portion 23. During use, wicking portion 23 transfers fluid from the wound W into reservoir 40. Preferably, reservoir 40 fits snugly against the sidewall defined by hydrophobic portion 22, so as to inhibit leakage of fluid in the reservoir out of the lateral face of the reservoir. Optionally, a layer of adhesive may be disposed on the lower surface of the reservoir 40 that engages ledge 28 of wicking portion 23 to removably secure those components together. Reservoir 40 preferably includes one or more vents 45 that assist in modulating the humidity within the dressing through cover 50. In some embodiments, a plurality of perforations P' are optionally defined in reservoir 40, along which a caregiver may tear reservoir 40 to resize the reservoir so as to better fit support cushion 20, which itself also may optionally be resized, as described herein.

Cover 50, preferably a breathable material, such as breathable foam or cloth, overlays reservoir 40. Layer 51 of adhesive preferably is used to removably secure reservoir 40 to cover 50. Alternatively, reservoir 40 may be removably fastened to cover 50 using a removable fastening system, such as hook and pile arrangement, or a repositionable adhesive. The cover 50 may retain reservoir 40 in engagement with wicking portion 23.

As described in greater detail below, the components of dressing 10 may each be provided with one or more non-stick liners to facilitate handling of the different components of the system, e.g., while placing support cushion 20 on epidermis E and/or while placing reservoir 40 on support cushion 20. The liners may be removed as appropriate to expose the adhesive layers and secure components to epidermis E or to each other.

Multiple features of dressing 10 both protect and enhance the healing of wound W. First, support cushion 20 is constructed to reduce or eliminate lateral forces applied to the surrounding epidermis that otherwise may cause dehiscence of the wound. For example, the support cushion 20 may be constructed of a high density foam of sufficient thickness to provides a rigid surround that protects the wound both from lateral and vertical forces, e.g., forces that would otherwise potentially cause wound dehesience by pulling the edges of the wound away from each other. Moreover, the optional perforations P may define support cushion 20 into two interlocking "J"-shaped portions that prevent or inhibit the wound from being pulled apart. The lateral offset of the junctions between the two J-shapes further enhances the support cushion's resistance to lateral forces.

Additionally, in some embodiments, additional optional perforations P allow specific portions of support cushion 20 to be removed, thus enabling a caregiver to adjust support cushion 20 to better fit around a particular wound. The shape and locations of perforations P preferably are configured to maintain the support cushion's resistance to lateral forces. For example, as illustrated in FIG. 3A, perforations P may be defined in support cushion 20 such that a portion of the perforations are laterally curved, e.g., the portions of the perforations extending through hydrophobic portion 22. If a caregiver removes sections 31 and 32 of support cushion 20 by tearing support cushion along the perforations P that bound those sections, then the remaining portions of support cushion will fit together along the curves defined by such removal and interlock with one another, resulting in the support cushion having a lateral strength comparable to its strength before the sections were removed. In other embodiments, the perforations P may be straight, or may be shaped, e.g., in the form of grooves, zig-zags, "U" shapes, or the like. For example, the perforations P may be angled, square, triangular, curved, or free form. The perforations P may define ends that interlock with one another to resist lateral separation from one another along the major and/or minor axes.

In the embodiment illustrated in FIG. 3A, optional perforations P are arranged as inverted mirror images of each other about the center of support cushion 20. Thus, if a caregiver removes sections 31 and 32 of support cushion 20 by tearing it along the perforations P bounding those sections, then support cushion 20 becomes separated into two "J"-shaped sections that may be rejoined and interlocked on epidermis E. In such embodiments, the offset of the junctions between the "J" helps to protect the wound from lateral forces, thus inhibiting dehiscence of the wound. Alternatively, perforations P may be arranged as mirror images of each other about the center of support cushion 20, e.g., a caregiver's removal of sections of support cushion 20 separates the support cushion into two "U"-shaped portions that may be rejoined and interlocked on epidermis E. Other configurations are possible, as described below.

Additionally, although reservoir 40 is arranged to protect the wound W from the environment and to absorb fluid, it is suspended over and thus is not in continuous contact with the wound. This feature may both reduce any pain experienced by the patient and promote healing. For example, initially placing reservoir 40 (and the other components of dressing 10) does not require touching the wound bed itself, resulting in significantly less pain than, for example, conventional dressings in which gauze is placed onto the wound. Support cushion and/or reservoir 40 also readily may be removed without disrupting re-epithelialization of the wound. Moreover, because reservoir 40 sequesters fluid from the wound, when reservoir 40 is removed to observe the wound, the fluid does not flow onto the adhesive used to secure cover 50 to support cushion 20. This arrangement allows reservoir 40 and cover 50 to be repositioned and re-secured to support cushion 20, without having to replace the entire dressing. By contrast, removing previously known dressings (which contact the wound) often disrupts re-epithelialization, and fluid within the dressing will flow onto the adhesive, requiring the entire dressing to be discarded and a new one applied. Alternatively, if reservoir 40 is saturated with fluid or if the caregiver identifies another reason to replace the reservoir, reservoir 40 and cover 50 may be replaced without having to remove the support cushion 20, thus reducing or avoiding trauma to the wound potentially associated with removal of support cushion 20.

It is noted that although reservoir 40 is designed to be suspended over, rather than in contact with the wound, occasions may arise where the reservoir will contact the wound. For example, if sufficient pressure is applied directly onto cover 50 and reservoir 40, the reservoir may deflect sufficiently to contact the wound for as long as that pressure is applied. Such temporary contact is not believed to significantly impede the healing of the wound, and the diameter and resiliency of support cushion 20 preferably are selected to provide adequate support for cover 50 and reservoir 40 in the expected range of applications.

Overview of Method

Figure 2:
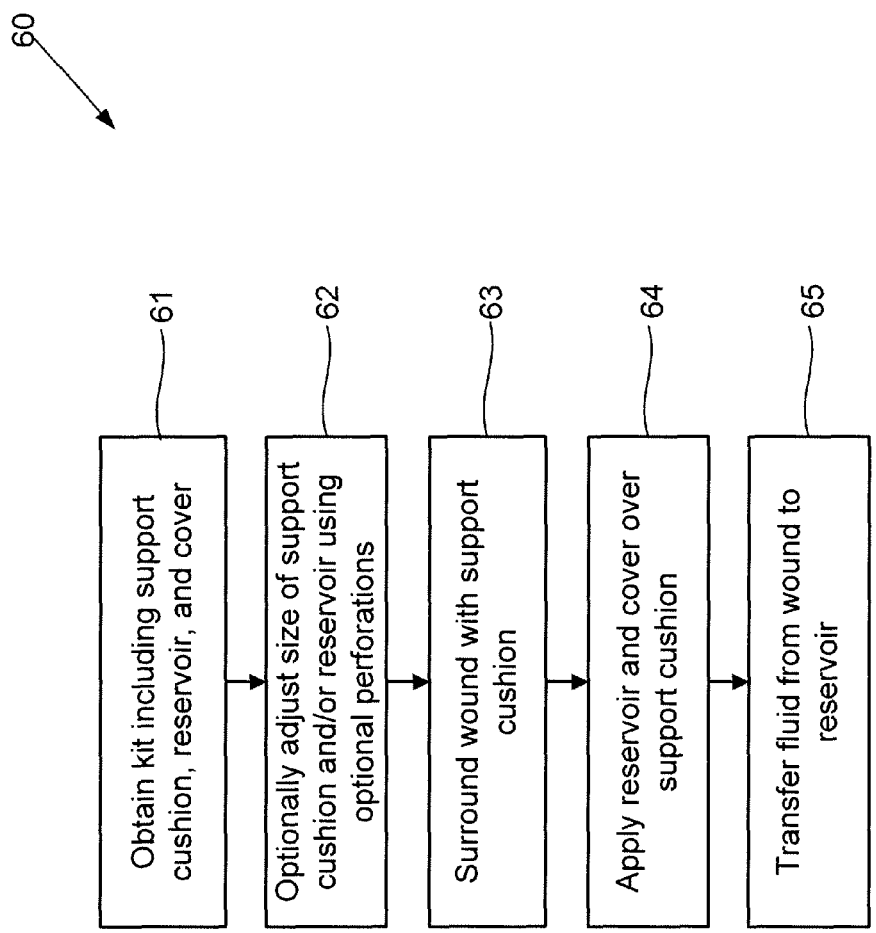
FIG. 2 illustrates steps in accordance with one method for protecting incisions.

FIG. 2 illustrates steps in a method 60 of using dressing 10 for managing exudate from a wound, according to some embodiments of the invention. Typically, the method is implemented by a physician, nurse, or other caregiver. However, the method is relatively simple to employ, and the patient himself or herself may apply dressing 10.

First, at step 61, the caregiver obtains support cushion 20, reservoir 40, and cover 50, e.g., a kit as described below with respect to FIGS. 5A-5B. Next, in step 62, the caregiver optionally adjusts the size of support cushion 20 and reservoir 40 to more closely circumscribe the wound. For example, as described in greater detail below, support cushion 20 and reservoir 40 optionally include perforations P, P' allowing the caregiver to remove selected portions of the respective component. Next, in step 63, support cushion 20 is applied to the epidermis of a patient, so that the support cushion surrounds the wound and a region of the epidermis surrounding the wound. In some embodiments, the wicking portion 23 surrounds the wound, and the hydrophobic portion 22 surrounds the wicking portion. In one example, a non-stick liner covering lower surface 24 of support cushion 20 may be removed to expose the adhesive on its lower surface. The support cushion then is roughly centered around the wound, and pressed onto the patient's epidermis using gentle manual pressure. A non-stick liner covering layer 27 on the upper surface of support cushion 20 may be left in place until a later step, described below.

At step 64, reservoir 40 and cover 50 (which is preferably pre-adhered to reservoir 40) then are applied over support cushion 20. For example, the non-stick liner may be removed from layer 27 disposed on the upper surface 26 of hydrophobic portion 22, and reservoir 40 inserted into support cushion 20 so that the exposed adhesive on support cushion 20 adheres to cover 50, as illustrated in FIG. 1B. Alternatively, layer 27 may be disposed on the lower surface of cover 50 and covered with a non-stick liner that may be removed so that the exposed adhesive on cover 50 adheres to the upper surface 26 of hydrophobic portion 22.

At step 65, fluid is transferred from the wound to the reservoir, e.g., via wicking portion 23.

Optionally, a medication or other substance may be applied to the wound or surrounding epidermis during any appropriate step in method 60. For example, the wound and epidermis may be cleaned, dried, and/or debrided or moisturized before applying support cushion 20 to the epidermis. Or, for example, medications, such as time-release topical medications, or special dressings, may be applied.

Further details of the construction of the individual components of dressing 10, and alternative embodiments, are now provided.

Support Cushion 20

Referring to FIG. 3A, a first embodiment of support cushion 20 is further described. Support cushion 20 includes sidewalls 30 defining a major axis and a minor axis, and optionally including at least two perforations P that traverse the sidewalls 30 at offset locations. The perforations P separate the support cushion 20 into first and second interlocking portions, e.g., "J"-shaped portions. In the illustrated embodiment, hydrophobic portion 22 define sidewalls 30; wicking portion 23 defines a flange, the upper surface 28 of which defines a ledge that contacts a portion of reservoir 40; and hydrophobic portion 22 and wicking portion 23 are secured to hydrophobic barrier 24 (not visible in FIG. 3A). Support cushion 20 preferably is secured to patient's epidermis using a biocompatible adhesive layer (also not visible in FIG. 3A), which is preferably hydrophobic but breathable. Alternatively, or additionally, support cushion 20 may be secured to the patient's epidermis using a covering material, such as gauze.

In some embodiments, support cushion 20 is of unitary construction, with hydrophobic portion 22, wicking portion 23, and hydrophobic barrier 24 all being formed from different portions of the same piece of material, which portions may be differently treated to modify their hydrophobicity/hydrophilicity as appropriate. Alternatively, one or more of hydrophobic portion 22, wicking portion 23, and hydrophobic barrier 24 may be individually constructed and then heat-fused or otherwise bonded together, e.g., using adhesive, thus allowing the materials, thicknesses, and other characteristics of hydrophobic portion 22, wicking portion 23, and hydrophobic barrier 24 to be tailored for specific applications. For example, it may be preferable to form hydrophobic portion 22 using a relatively thick layer of a large-cell hydrophobic material, to form wicking portion 23 using a relatively thin layer of a small-cell hydrophobic material, and to form hydrophobic barrier 24 using a relatively thin layer of large-cell hydrophobic material. Such a combination of materials and thicknesses imparts support cushion 20 with sufficient flexibility to be conformable to substantially any body part, e.g., an arm, leg, neck, or torso, while maintaining a sufficient level of hydrophobicity to prevent fluids from leaking out of the support cushion and onto the epidermis.

Examples of suitable hydrophobic materials for use in hydrophobic portion 22 and hydrophobic barrier 24 include polyolefins, foams (for example, polyethylene foams), and silicone-based materials, in open cell, closed cell, large cell, or small cell forms. In still other embodiments (not illustrated), hydrophobic portion 22 and/or hydrophobic barrier 24 may be configured as an annular structure filled with a fluid, e.g., air or water, a gel, an expanded plastic, or fibers. Such structure may be formed of molded plastic, welded polymer, or a laminate. One example of a suitable hydrophilic, flexible material for use in wicking portion 23 is an open-cell foam such as hydrophilic polyurethane. Alternatively, wicking portion may include any suitable absorbent structure, e.g., a woven fabric, a nonwoven fabric, a hydrogel (which may include modified starch), or a pouch filled with a polymeric absorbent material. Any suitable adhesive or bonding procedure can be used to adhere hydrophobic portion 22, wicking portion 23, and hydrophobic barrier 24 together.

In the embodiment illustrated in FIG. 3A, support cushion 20 is pre-formed in a generally rectangular shape, and is suitable for use with wounds up to a fixed size, e.g., up to 30 mm in length, or up to 6" in length. Support cushion 20 also may have a plurality of perforations P defined therein, dividing support cushion 20 into at least two interlocking portions, e.g., into two "J"-shaped portions. Optionally, a plurality of additional perforations P may be defined in support cushion 20 that are configured to enable removal of specified portions of the support cushion, e.g., portions 31 and 32, by tearing the support cushion along one or more of the perforations, and are also configured to allow the remaining portions of the support cushion 20 to interlock with one another, thus allowing the size of opening 29 to be reduced to more closely circumscribe the wound. In one embodiment, the perforations P are provided at ½" intervals, allowing support cushion 20 to be shortened in ½" increments.

Alternatively, as illustrated in FIG. 3D, support cushion 20''' optionally may be pre-formed to include perforations enabling the support cushion to be separated into separate portions, and additional sections 33, 34 of support cushion material may be provided to increase the size of opening 29. The additional sections 33, 34 of support cushion material may be provided to the caregiver in strips that include a plurality of such sections, which are separable from one another by tearing along perforations. In one example, the sections are provided in ½" lengths, allowing any desired multiple of ½" lengths to be added to lengthen support cushion 20'''. Support cushion 20 alternatively may be formed in any other appropriate shape and size and may be provided having a range of size of openings 29. For example, support cushion 20 may be pre-formed in a generally circular, rectangular, triangular, or other polyhedral shape, optionally having curved corners, or may even be pre-formed in an irregular shape.

In the embodiment of FIGS. 1A-1B and 3A, wicking portion 23 is depicted as being thinner (shorter) than hydrophobic portion 22, so as to define a recess into which reservoir 40 snugly fits. For example, in some embodiments, the height of wicking portion 23 is in a range of 40-60% of the height of the hydrophobic portion 22. However, wicking portion 23 actually may have the same thickness (height) as hydrophobic portion 22, and reservoir 40 may compress the wicking portion 23 to a shorter height than hydrophobic portion 22 during use. For example, in the alternative support cushion 20' illustrated in FIG. 3B, wicking portion 23' is as thick (as tall) as hydrophobic portion 22, but has a different compliance, e.g., is more easily compressed. Thus, during use, reservoir 40 may engage the upper surface 28' of wicking portion 23', and compress the wicking portion to a thickness (height) such that cover 50 contacts adhesive 27 on the top surface 26 of hydrophobic portion 22, and reservoir 40 fits snugly within hydrophobic portion 22. In other embodiments (not illustrated), wicking portion 23' may even be thicker (taller) than hydrophobic portion 22.

Additionally, not all embodiments require hydrophobic barrier 24. For example, in the alternative support cushion 20" illustrated in FIG. 3C, hydrophobic portion 22" and wicking portion 23" both are adhered to the epidermis E via adhesive layer 25". In the embodiment illustrated in FIG. 3C, wicking portion 23" is thinner (shorter) than hydrophobic portion 22". However, as discussed above with respect to FIG. 3B, wicking portion 23" alternatively may be as thick as, or even thicker than, hydrophobic portion 22".

Reservoir 40

As illustrated in FIGS. 1A-1B, reservoir 40 may include multiple layers bonded together or alternatively may be formed of a single, hydrophilic layer. In the embodiment of FIG. 1, reservoir 40 includes upper layer 43, lower layer 41 and intervening layer 42. Lower layer 41 engages the upper surface 28 of wicking portion 23, and transfers fluid through intervening layer 42, and into upper layer 43. Although reservoir 40 is composed of breathable materials that allow for the transfer of moisture vapor as needed, reservoir 40 optionally may contain one or more vents 45 that extend through the reservoir to improve moisture vapor transfer through cover 50. For example, there may be one, two, three, or more than three vents 45 extending through reservoir 40.

Referring again to FIG. 1B, both upper layer 43 and lower layer 41 are hydrophilic. However, layers 41 and 43 may have the same or different hydrophilicities, mechanical properties, transfer rates for fluid, and capacities for absorbing fluid. In some embodiments, layers 41 and 43 are formed from hydrophilic polyurethane foams, e.g., commercially purchased polyurethane foams from Rynel, Inc. (Wicasset, Me., USA). The foam from which lower layer 41 is fabricated has a higher hydrophilicity than that of upper layer 43, allowing it to rapidly transfer exudate into upper layer 43. The polyurethane foams may be coated or interlaced with any suitable antibacterial, wound healing, or antimicrobial agents (e.g., silver) to combat or prevent infection.

Intervening layer 42 enhances the strength and stiffness of reservoir 40, making it more difficult to inadvertently deflect reservoir 40 downward to contact the wound and inhibiting potential collapse of the reservoir into contact with the wound. Intervening layer 42 may be, for example, a substantially non-stretchable mesh or scrim, such as a metallic, nylon, or polyester-based mesh.

As discussed herein, in some embodiments support cushion 20 has optional perforations defined therein that allow specified sections of the support cushion to be removed. In such embodiments, it may be advantageous to also provide perforations P' in reservoir 40, thus allowing portions of the reservoir 40 to be removed by tearing the reservoir along the perforations, e.g., to remove portions 46 and 47. In this manner, reservoir 40 may be resized as needed to fit snugly over the wicking portion 23 of support cushion 20. In one example, the perforations P' are provided at intervals that are one-half the length of the intervals for perforations P, e.g., P' are perforated at ¼" intervals when P are perforated at ½" intervals.

Cover 50

Referring now to FIGS. 1B and 4, cover 50 is described having pre-fastened reservoir 40 with vent 45. Cover 50 may be adhered to upper layer 43 with a layer of adhesive, or otherwise attached to upper layer 43 before or after reservoir 40 is placed over the wound. Preferably, cover 50 is not attached to those sections of reservoir 40 that are configured for optional removal using perforations P'.

During use, cover 50 is adhered to the upper surface of hydrophobic portion 22 using layer 27 of adhesive, for example a biocompatible adhesive, which urges reservoir 40 against wicking portion 23. In other embodiments, layer 27 may comprise a removable fastener, such as a hook and pile arrangement or a repositionable adhesive that enables the cover 50 and reservoir 40 to be periodically removed to inspect the wound, apply medicaments, and/or to replace the reservoir 40 without entirely removing the dressing, e.g., without removing the support cushion 20.

In some embodiments, cover 50 extends beyond the lateral dimensions of support cushion 20, so that when dressing 10 is applied to a patient, cover 50 drapes over support cushion 20 and covers layer 27 of adhesive. Such draping protects the edges of support cushion 20 from lifting, and additionally provides a smooth, comfortable surface over which clothing and bed linens may slide freely.

Cover 50 is made of a soft, occlusive material that provides an antibacterial barrier between the wound W and the environment, and also allows humidity to escape from reservoir 40 and vent 45. One example of a suitable material for cover 50 is Intelicoat 5243, available from Intelicoat Technologies (South Hadley, Mass., USA). Other suitable materials include foams, wovens, and nonwovens. The material may be coated or intercalated with any suitable antibacterial or antimicrobial agent to combat or prevent infection.

Kits

The components of a dressing constructed in accordance with the principles of the present invention, illustratively dressing 10 of FIGS. 1A-1B, may be provided to patients or caregivers as a kit 70, illustrated in FIG. 5A. Kit 70 includes a cardboard or other sturdy, disposable backing 71 upon which support cushion 20, reservoir 40, and cover 50 are removably mounted. Examples of alternative disposable backings 71 include dark, colored or translucent trays of materials such as polystyrenes (for example available from Sealed Air Corp., Elmwood Park, N.J., USA; or Perfecseal®, a BEMIS Co., Oshkosh, Wis., USA; or Universal Plastics Corp., Holyoke, Mass., USA). Kit 70 may also include additional components, e.g., different sizes and shapes of support cushion 20, reservoir 40, and/or cover 50, or portions of support cushion 20 and/or reservoir 40 that may be inserted in those components to increase their size, to be able to accommodate different sizes and shapes of wounds (not illustrated). In an alternative embodiment, the components of dressing 10 are instead provided in one or more compartments of a tray.

In the illustrated embodiment, pieces of excess material adhered to backing 71 may be used to secure the components of dressing 10 to backing 71 until they are needed. For example, opening 29 in support cushion 20 may be formed by cutting piece 73 from one or layers of the material from which the support cushion is formed (e.g., the material from which wicking portion 23 is formed, and/or the material from which hydrophobic barrier 24 is formed, and/or the material from which hydrophobic portion 22 is formed), and then adhering that piece 73 to backing 71. Because piece 73 snugly fits into the hole of support cushion 20, friction between piece 73 and support cushion 20 serves to removably retain support cushion 20 on backing 71 without the need for additional adhesive or tabs, until removed by the patient or caregiver. Similarly, reservoir 40 may be cut from the center of a larger piece 74 that is subsequently adhered to backing 71. Friction between reservoir 40 and piece 74 retains reservoir 40 frictionally engaged on backing 71 without the need for additional adhesive or tabs, until removed for use. Any other material may be used to frictionally engage reservoir 40 and/or support cushion 20 on backing 71. Alternatively, as illustrated in FIG. 5B, in kit 70' foldable tabs 72 cut from backing 71 may be used to secure some or all of the components onto backing 71.

Referring again to FIG. 5A, instructions for use 75 for applying the different components of dressing 10 to a patient may be printed on backing 71, e.g., instructions for implementing the method described with respect to FIG. 2. Alternatively, instructions may be printed on the packaging medium. The instructions may be sterilized so that they may be safely used in a sterilized field, such as an operating room. The adhesive layers on the different components are covered with non-stick, removable liners that may be color coded or have a series of perforations or symbols to guide the patient or caregiver in determining the order in which to apply the components of dressing 10. Such non-stick liners may facilitate handling of the different components of dressing 10, e.g., while placing support cushion 20 on the patient's epidermis.

Kit 70 preferably further includes a pouch (not shown) in which backing 71 and dressing 10 are sealed until needed. Preferably, the pouch is transparent on at least its upper surface, allowing backing 71 and the other components to be viewed. Additionally, instructions for use 75 may be located on backing 71 so as to make possible reading of the instructions before opening the pouch. The pouch also may be constructed to aid retention of the components of dressing 10 on backing 71. Kit 70 preferably is sterilizable, e.g., may be sterilized after assembly, such that the contents of the pouch remain sterile until it is opened, e.g., immediately before the dressing is applied to a patient. The pouch preferably comprises a material that retains its integrity during conventional sterilizing procedures, e.g., exposure to gamma radiation, an electron beam, hydrogen peroxide, or ethylene oxide gas.

It is envisioned that a typical wound care treatment environment, such as a hospital, wound care outpatient clinic or doctor's office, may stock an inventory of kits 70 designed for use with different sizes or shapes of wounds. For example, a plurality of kits 70 may be manufactured having support cushion 20, reservoir 40, and cover 50 in a variety of sizes and shapes, according to different wound sizes and shapes with which they may be suitable for use. Alternatively, or in addition, individual components of the dressing, such as the reservoirs, may be individually packaged, for example to permit periodic replacement of the reservoir with greater frequency than the dressing as a whole.

Alternative Configurations

As noted above, support cushions and reservoirs suitable for use in the inventive dressing may be configured to accommodate different shapes and sizes of wounds. For example, FIGS. 6A and 6B illustrate an alternative dressing in which a support cushion 80 and reservoir 85 include perforations enabling removal of selected portions of these components both along the minor axis and along the major axis. Specifically, like support cushion 20 described above, alternative support cushion 80 includes perforations P that enable removal of selected portions of the support cushion along the major axis to reduce a length of the support cushion along the major axis, e.g., removal of portions 31 and 32. Support cushion 80 additionally includes perforations PA that enable removal of selected portions of the support cushion along the minor axis to reduce a width of the support cushion along the minor axis, e.g., removal of portions 81 and 82. Similarly, like reservoir 40 described above, alternative reservoir 85 includes perforations P' that enable removal of selected portions of the reservoir along the major axis to reduce a length of the reservoir along the major axis, e.g., removal of portions 46' and 47'. Reservoir 85 also includes perforations PA' that enable removal of selected portions of the reservoir along the minor axis to reduce a width of the reservoir along the minor axis, e.g., removal of portions 48 and 49.

It should be noted that in still other embodiments, support cushion 80 and/or reservoir 85 may only include perforations enabling removal of selected portions of these components along the minor axis, e.g., include perforations PA and PA', but not perforations P and P'.

Additionally, as noted above, dressings may be formed in shapes other than rectangular. For example, as illustrated in FIG. 7, in one alternative embodiment support cushion 90, reservoir 95, and cover 96 are elliptically shaped. Support cushion 90 includes sidewalls 99 defining a major axis and a minor axis, and optionally including at least two perforations PB that traverse the sidewalls at offset locations, thus dividing support cushion 90 into two asymmetrical "C"-shaped portions that interlock with one another. Optionally, support cushion 90 includes additional perforations PB that enable removal of selected portions of the support cushion along the major axis to reduce a length of the support cushion along the major axis, e.g., removal of portions 91 and 92. Reservoir 95 includes optional vent holes 45, which may be the same as the vent holes 45 described above, and optionally also includes perforations PB' that enable removal of selected portions of the reservoir along the major axis to reduce a length of the reservoir along the major axis, e.g., removal of portions 93 and 94. Note that because of the curvature of support cushion 90 and reservoir 95, both the length and the width of these components may be reduced when portions are removed.

While various illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed:

1. A dressing for protecting a wound, the dressing comprising:
    a support cushion configured to surround the wound, the support cushion having sidewalls defining a major axis and a minor axis, the support cushion including at least two perforations that traverse the sidewalls at offset locations, the perforations defining first and second J-shaped portions of the support cushion, each J-shaped portion having a first end with a shape and a second end that fits together with the shape, the first end of the first J-shaped portion interlocking with the second end of the second J-shaped portion and the second end of the first J-shaped portion interlocking with the first end of the second J-shaped portion to resist lateral separation of the first and second J-shaped portions from one another along at least one of the major axis and the minor axis;
    a reservoir configured to be suspended over and in engagement with the support cushion; and
    a cover configured to be positioned over the reservoir.

2. The dressing of claim 1 wherein the support cushion comprises a hydrophobic portion and a wicking portion, the wicking portion being configured to surround the wound and the hydrophobic portion being configured to surround the wicking portion.

3. The dressing of claim 2 wherein the wicking portion is configured to transfer fluid from the wound to the reservoir.

4. The dressing of claim 2, wherein the cover is configured to retain the reservoir in engagement with the wicking portion.

5. The dressing of claim 2, wherein the wicking portion defines a flange of the support cushion, the flange having a ledge to accept a portion of the reservoir.

6. The dressing of claim 1, wherein the support cushion includes additional perforations that enable removal of selected portions of the support cushion along the major axis to reduce a length of the support cushion along the major axis.

7. The dressing of claim 1, wherein the support cushion includes additional perforations that enable removal of selected portions of the support cushion along the minor axis to reduce a width of the support cushion along the minor axis.

8. The dressing of claim 1, wherein at least a portion of each of the at least two perforations is curved.

9. The dressing of claim 1, further comprising a plurality of perforations defined in the reservoir to enable removal of selected portions of the reservoir.

10. The dressing of claim 1, wherein the support cushion further comprises a hydrophobic barrier.

11. The dressing of claim 1, further comprising a biocompatible adhesive for securing the support cushion around the wound.

12. The dressing of claim 1, wherein the reservoir comprises a first hydrophilic layer, a non-stretchable mesh or scrim, and a second hydrophilic layer.

13. The dressing of claim 1, wherein the cover comprises a breathable material.

14. The dressing of claim 13, wherein a vent is defined in the reservoir, the vent permitting humidity over the wound to escape through the vent and the cover.

15. The dressing of claim 1, further comprising a biocompatible adhesive securing the cover to the reservoir.

16. The dressing of claim 1, further comprising a biocompatible adhesive for securing the cover to the support cushion.

17. The dressing of claim 1, further comprising means for repeatedly attaching and detaching the cover to the support cushion so that the wound is viewable without entirely removing the dressing.

18. A method for protecting a wound, the method comprising:
    providing a support cushion configured to surround the wound, the support cushion having sidewalls defining a major axis and a minor axis, the support cushion including at least two perforations that traverse the sidewalls at offset locations, the perforations defining first and second J-shaped portions of the support cushion, each J-shaped portion having a first end with a shape and a second end that fits together with the shape, the first end of the first J-shaped portion interlocking with the second end of the second J-shaped portion and the second end of the first J-shaped portion interlocking with the first end of the second J-shaped portion to resist lateral separation of the first and second J-shaped portions from one another along at least one of the major axis and the minor axis;
    surrounding the wound with a support cushion;
    applying a reservoir over the support cushion; and
    transferring fluid from the wound to the reservoir.

19. The method of claim 18, wherein a plurality of additional perforations are defined in the support cushion, the method further comprising reducing a size of the support cushion along the major axis by removing selected portions of the support cushion.

20. The method of claim 18, wherein the reservoir includes a plurality of perforations, the method further comprising reducing a size of the reservoir by removing a selected portion of the reservoir along at least one perforation of the plurality of perforations defined in the reservoir.

21. The method of claim 18, wherein the support cushion includes a stepped profile that defines a ledge and a recess, the method further comprising fitting the reservoir within the recess so that the reservoir engages the ledge and is suspended over the wound.

22. The method of claim 21, wherein the support cushion comprises a hydrophobic portion that defines the recess and a hydrophilic portion that defines the ledge.

23. The method of claim 18, further comprising securing a cover to the support cushion with a biocompatible adhesive.

24. A kit for a dressing for use in protecting a wound, the kit comprising:
    a support cushion configured to surround the wound, the support cushion having sidewalls defining a major axis and a minor axis, the support cushion including at least two perforations that traverse the sidewalls at offset locations, the perforations defining first and second J-shaped portions of the support cushion, each J-shaped portion having a first end with a shape and a second end that fits together with the shape, the first end of the first J-shaped portion interlocking with the second end of the second J-shaped portion and the second end of the first J-shaped portion interlocking with the first end of the second J-shaped portion to resist lateral separation of the first and second J-shaped portions from one another along at least one of the major axis and the minor axis;

a reservoir configured to be applied over the support cushion;
a backing upon which the support cushion and reservoir are mounted; and
instructions for use printed on the backing, the instructions for use describing steps for assembling the dressing.

* * * * *